(12) United States Patent
Kamei et al.

(10) Patent No.: US 11,828,755 B2
(45) Date of Patent: Nov. 28, 2023

(54) BIOMARKER CONCENTRATION AND SIGNAL AMPLIFICATION FOR USE IN PAPER-BASED IMMUNOASSAYS AND A SINGLE PLATFORM FOR EXTRACTING, CONCENTRATING, AND AMPLIFYING DNA

(71) Applicant: The Regents of the University of California, Oakland, CA (US)

(72) Inventors: Daniel Takashi Kamei, Monterey Park, CA (US); Benjamin Ming Wu, San Marino, CA (US); Daniel William Bradbury, Los Angeles, CA (US); Shin Ting Sherine Frieda Cheung, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 847 days.

(21) Appl. No.: 16/307,125

(22) PCT Filed: Jun. 7, 2017

(86) PCT No.: PCT/US2017/036418
§ 371 (c)(1),
(2) Date: Dec. 4, 2018

(87) PCT Pub. No.: WO2017/214315
PCT Pub. Date: Dec. 14, 2017

(65) Prior Publication Data
US 2019/0250156 A1    Aug. 15, 2019

Related U.S. Application Data

(60) Provisional application No. 62/348,038, filed on Jun. 9, 2016.

(51) Int. Cl.
G01N 33/543 (2006.01)
C12Q 1/6844 (2018.01)
C12Q 1/6813 (2018.01)

(52) U.S. Cl.
CPC ..... *G01N 33/54388* (2021.08); *C12Q 1/6813* (2013.01); *C12Q 1/6844* (2013.01); *G01N 33/543* (2013.01); *G01N 33/54306* (2013.01)

(58) Field of Classification Search
CPC ....... G01N 33/54386; G01N 33/54387; G01N 33/54388; G01N 33/54389;
(Continued)

(56) References Cited

U.S. PATENT DOCUMENTS 5,141,850 A    8/1992 Cole et al.
6,194,221 B1    2/2001 Rehg et al.
(Continued)

FOREIGN PATENT DOCUMENTS

CN    106662582 A    5/2017
EP    1064553 A1    1/2001
(Continued)

OTHER PUBLICATIONS

EP Extended Search Report dated Mar. 23, 2021 issued in EP 20200335.6.
(Continued)

*Primary Examiner* — Christopher L Chin
(74) *Attorney, Agent, or Firm* — Tom Hunter; Weaver Austin Villeneuve & Sampson LLP

(57) ABSTRACT

In various embodiments methods and devices are provided for the detection and/or quantification of an analyte. In certain embodiments a device is provided comprising an aqueous two-phase system (ATPS) comprising a mixed phase solution that separates into a first phase solution and a second phase where, in use, said first phase solution becomes a leading phase and said second phase solution becomes a lagging phase; a lateral-flow assay (LFA); and a probe and/or a development reagent, where in use, said probe associates with said first phase solution in said leading phase of said ATPS and/or said development reagent associates with said second phase solution in said lagging phase of said ATPS. In certain embodiments a "one-pot" system of purifying and amplifying a nucleic acid is provided utilizing, e.g., an ATPS and isothermal amplification reagents.

23 Claims, 11 Drawing Sheets

(58) Field of Classification Search
CPC ........... G01N 33/54391; G01N 33/543; G01N 33/54306; G01N 33/558; B01L 2300/0825; C12Q 2565/625
USPC ....... 422/400, 401, 420, 421, 425, 426, 430; 435/287.7, 287.9, 970, 805, 810; 436/169, 170, 514, 518, 530, 810
See application file for complete search history.

(56) References Cited

U.S. PATENT DOCUMENTS

| | | |
|---|---|---|
| 6,855,561 B2 | 2/2005 | Jerome et al. |
| 6,924,153 B1 | 8/2005 | Boehringer et al. |
| 6,979,576 B1 | 12/2005 | Cheng et al. |
| 7,179,657 B2 | 2/2007 | Jerome et al. |
| 7,226,793 B2 | 6/2007 | Jerome et al. |
| 7,459,314 B2 | 12/2008 | Guo et al. |
| 7,537,937 B2 | 5/2009 | Jerome et al. |
| 7,553,675 B2 | 6/2009 | Jerome et al. |
| 7,666,614 B2 | 2/2010 | Cheng et al. |
| 7,794,656 B2 | 9/2010 | Liang et al. |
| 7,867,780 B2 | 1/2011 | Jones et al. |
| 7,932,099 B2 | 4/2011 | Egan et al. |
| 8,003,765 B2 | 8/2011 | Pentyala et al. |
| 8,030,091 B2 | 10/2011 | Jerome et al. |
| 8,193,002 B2 | 6/2012 | Guo et al. |
| 8,377,710 B2 | 2/2013 | Whitesides et al. |
| 8,445,293 B2 | 5/2013 | Babu et al. |
| 8,603,832 B2 | 12/2013 | Whitesides et al. |
| 8,628,729 B2 | 1/2014 | Carrilho et al. |
| 8,828,739 B2 | 9/2014 | Guo et al. |
| 9,193,988 B2 | 11/2015 | Whitesides et al. |
| 9,207,236 B2 | 12/2015 | Cary |
| 9,250,236 B2 | 2/2016 | Babu et al. |
| 9,347,955 B2 | 5/2016 | Pieribone |
| 9,823,247 B2 | 11/2017 | Kamei et al. |
| 10,006,911 B2 | 6/2018 | Kamei et al. |
| 10,359,423 B2 | 7/2019 | Kamei et al. |
| 10,578,616 B2 | 3/2020 | Kamei et al. |
| 11,209,427 B2 | 12/2021 | Kamei et al. |
| 11,287,426 B2 | 3/2022 | Kamei et al. |
| 11,327,075 B2 | 5/2022 | Kamei et al. |
| 2003/0215358 A1 | 11/2003 | Schulman et al. |
| 2004/0002168 A1 | 1/2004 | Remington et al. |
| 2004/0203079 A1 | 10/2004 | Pentyala et al. |
| 2004/0214171 A1 | 10/2004 | Yamashita et al. |
| 2005/0239216 A1 | 10/2005 | Feistel |
| 2006/0019406 A1 | 1/2006 | Wei et al. |
| 2006/0025579 A1 | 2/2006 | Riedl et al. |
| 2007/0003992 A1 | 1/2007 | Pentyala et al. |
| 2007/0140911 A1 | 6/2007 | Carney et al. |
| 2007/0196864 A1 | 8/2007 | Pentyala et al. |
| 2007/0292902 A1 | 12/2007 | Cheng et al. |
| 2008/0138842 A1 | 6/2008 | Boehringer et al. |
| 2008/0227113 A1 | 9/2008 | Pentyala et al. |
| 2008/0227220 A1 | 9/2008 | Franse et al. |
| 2008/0254440 A1 | 10/2008 | Uchida et al. |
| 2009/0110601 A1 | 4/2009 | Levi et al. |
| 2009/0191648 A1 | 7/2009 | Bohannon |
| 2010/0227323 A1 | 9/2010 | Baeumner et al. |
| 2011/0003310 A1 | 1/2011 | Ennis et al. |
| 2011/0072885 A1 | 3/2011 | Inana et al. |
| 2011/0151479 A1 | 6/2011 | Stevens et al. |
| 2011/0312074 A1 | 12/2011 | Azimi et al. |
| 2012/0107956 A1 | 5/2012 | Boehringer et al. |
| 2012/0238008 A1 | 9/2012 | Henry et al. |
| 2013/0065784 A1 | 3/2013 | Takayama et al. |
| 2013/0102063 A1 | 4/2013 | Levi et al. |
| 2013/0266956 A1 | 10/2013 | Tia et al. |
| 2014/0004539 A1 | 1/2014 | Simon et al. |
| 2014/0038222 A1 | 2/2014 | Alt et al. |
| 2014/0228549 A1 | 8/2014 | Schembecker et al. |
| 2015/0017656 A1 | 1/2015 | Wang |
| 2015/0099656 A1 | 4/2015 | Manuguerra et al. |
| 2015/0198592 A1 | 7/2015 | Wang |
| 2015/0253320 A1 | 9/2015 | Kamei et al. |
| 2015/0323534 A1 | 11/2015 | Egan et al. |
| 2016/0266119 A1 | 9/2016 | Sambursky et al. |
| 2016/0282343 A1 | 9/2016 | Jeyendran et al. |
| 2016/0313307 A1 | 10/2016 | Titmus et al. |
| 2016/0334397 A1 | 11/2016 | Yan et al. |
| 2017/0323441 A1 | 11/2017 | Shah et al. |
| 2018/0100854 A1 | 4/2018 | Kamei et al. |
| 2018/0188256 A1 | 7/2018 | Wong |
| 2018/0259521 A1 | 9/2018 | Kamei et al. |
| 2019/0033308 A1 | 1/2019 | Kamei et al. |
| 2019/0187140 A1 | 6/2019 | Kamei et al. |
| 2019/0391143 A1 | 12/2019 | Kamei et al. |
| 2020/0033336 A1 | 1/2020 | Kamei et al. |
| 2020/0124595 A1 | 4/2020 | Irudayaraj et al. |
| 2020/0150116 A1 | 5/2020 | Kamei et al. |
| 2020/0284791 A1 | 9/2020 | Kamei et al. |
| 2022/0146507 A1 | 5/2022 | Kamei et al. |
| 2022/0252598 A1 | 8/2022 | Kamei et al. |

FOREIGN PATENT DOCUMENTS

| | | |
|---|---|---|
| EP | 1340085 A1 | 9/2003 |
| EP | 1436592 A1 | 7/2004 |
| EP | 1733233 A2 | 12/2006 |
| EP | 1771734 A1 | 4/2007 |
| EP | 0941468 B1 | 7/2007 |
| EP | 2076775 A2 | 7/2009 |
| EP | 2126569 A2 | 12/2009 |
| EP | 2245135 A2 | 11/2010 |
| EP | 2426498 A1 | 3/2012 |
| JP | H03-130663 A | 6/1991 |
| JP | 2003-250575 A | 9/2003 |
| JP | 2007-500363 A | 1/2007 |
| JP | 2008-537119 A | 9/2008 |
| JP | 2011-075366 A | 4/2011 |
| JP | 2013-531259 A | 8/2013 |
| JP | 2013-181870 A | 9/2013 |
| KR | 20080103200 A | 11/2008 |
| WO | WO 98/018964 | 5/1998 |
| WO | WO 2004/081528 A2 | 9/2004 |
| WO | WO 2005/074609 A2 | 8/2005 |
| WO | WO 2005/098439 A2 | 10/2005 |
| WO | WO 2005/042579 A1 | 12/2005 |
| WO | WO 2007/092302 A2 | 8/2007 |
| WO | WO 2008/043040 A2 | 4/2008 |
| WO | WO 2011/116256 A2 | 9/2011 |
| WO | WO 2011/159537 A2 | 12/2011 |
| WO | WO 2012/010666 A1 | 1/2012 |
| WO | WO 2013/105090 A1 | 7/2013 |
| WO | WO 2015/134938 A1 | 9/2015 |
| WO | WO 2017/041030 A1 | 3/2017 |
| WO | WO 2017/214315 A1 | 12/2017 |
| WO | WO 2018/039139 A1 | 3/2018 |
| WO | WO 2018/183211 A1 | 10/2018 |
| WO | WO 2018/222765 A1 | 12/2018 |

OTHER PUBLICATIONS

KR Office Action dated Mar. 22, 2021 issued in KR 10-2016-7027705.
CN Second Office Action dated Feb. 20, 2021 issued in CN 201680059385.6.
JP Office Action dated Sep. 7, 2020 issued in JP 2018-511707.
EP Office Action dated Oct. 6, 2020 issued in EP 17810966.6.
EP Extended Supplementary Search Report dated Jan. 27, 2021 issued in EP 18809609.3.
U.S. Final Office Action dated Jun. 4, 2020 issued in U.S. Appl. No. 15/756,542.
U.S. Office Action dated Jan. 21, 2021 issued in U.S. Appl. No. 15/756,542.
U.S. Office Action dated Oct. 27, 2020 issued in U.S. Appl. No. 16/498,312.
Koczula, et al. (2016) "Lateral flow assays." *Essays in Biochemistry* 60: 111-120.
Mosley G. et al. (2017) "Improved lateral-flow immunoassays for chlamydia and immunoglobulin M by sequential rehydration of

(56) References Cited

OTHER PUBLICATIONS two-phase system components within a paper-based diagnostic" *Mikrochimica Acta* 184(10): 4055-4064.
Risch, et al. (2005) "Rapid, accurate and non-invasive detection of cerebrospinal fluid leakage using combined determination of β-trace protein in secretion and serum" *Clinica Chimica Acta* 351: 169-176.
PCT International Search Report and Written Opinion dated Jun. 3, 2015 issued in PCT/US2015/019297.
PCT International Preliminary Report on Patentability dated Sep. 13, 2016 issued in PCT/US2015/019297.
PCT International Search Report and Written Opinion dated Dec. 22, 2016 issued in PCT/US2016/050257.
PCT International Preliminary Report on Patentability dated Mar. 15, 2018 issued in PCT/US2016/050257.
PCT International Search Report and Written Opinion dated Sep. 20, 2017 issued in PCT/US2017/036418.
PCT International Preliminary Report on Patentability dated Dec. 20, 2018 issued in PCT/US2017/036418.
PCT International Search Report and Written Opinion dated Dec. 1, 2017 issued in PCT/US2017/047849.
PCT International Preliminary Report on Patentability dated Feb. 26, 2019 issued in PCT/US2017/047849.
PCT International Search Report and Written Opinion dated Aug. 3, 2018 issued in PCT/US2018/035204.
PCT International Preliminary Report on Patentability dated Dec. 3, 2019 issued in PCT/US2018/035204.
PCT International Preliminary Report and Written Opinion dated Jun. 15, 2018 issued in PCT/US2018/024392.
PCT International Preliminary Report on Patentability dated Oct. 1, 2019 issued in PCT/US2018/024392.
AU Examination report No. 1 dated Oct. 8, 2019 issued in AU 2015226930.
CN First Office Action dated Jan. 22, 2018 issued in CN 201580023439.9.
CN Second Office Action dated Nov. 29, 2018 issued in CN 201580023439.9.
EP Extended Search Report dated Oct. 26, 2017 issued in EP 15758881.5.
JP Office Action dated Feb. 8, 2019 issued in JP 2016-573716.
JP 2nd Office Action dated Feb. 3, 2020 issued in JP 2016-573716.
MY Office Action dated Dec. 2, 2019 issued in MY PI2016001615.
SG Office Action [Search Report and Written Opinion] dated Jan. 24, 2018 issued in SG 11201607582R.
SG Examination Report dated May 14, 2019 issued in SG 11201607582R.
CN First Office Action dated Mar. 27, 2020 issued in CN 201680059385.6.
EP Partial Supplementary Search Report dated Feb. 4, 2019 issued in EP 16843134.4.
EP Extended Supplementary Search Report dated Jun. 14, 2019 issued in EP 16843134.4.
EP Extended Supplementary Search Report dated Dec. 6, 2019 issued in EP 17810966.6.
U.S. Office Action dated Jan. 6, 2017 issued in U.S. Appl. No. 14/641,022.
U.S. Notice of Allowance dated Jul. 20, 2017 issued in U.S. Appl. No. 14/641,022.
U.S. Notice of Allowance dated Aug. 8, 2017 issued in U.S. Appl. No. 14/641,022.
U.S. Notice of Allowance dated Feb. 28, 2018 issued in U.S. Appl. No. 15/787,638.
U.S. Office Action dated Nov. 2, 2018 issued in U.S. Appl. No. 15/990,398.
U.S. Notice of Allowance dated Apr. 3, 2019 issued in U.S. Appl. No. 15/990,398.
U.S. Office Action [Restriction Requirement] dated May 14, 2019 issued in U.S. Appl. No. 15/756,542.
U.S. Office Action dated Sep. 26, 2019 issued in U.S. Appl. No. 15/756,542.

Ahmed (2015) "Hydrogel: Preparation, characterization, and applications: A review" *J. Adv. Res.*, 6:105-121.
Arrer et al. (2002) "β-Trace Protein as a Marker for Cerebrospinal Fluid Rhinorrhea" *Clin. Chem.* 48(6): 939-941.
Bachmann et al. (2002) "Predictive values of beta-trace protein (prostaglandin D synthase) by use of laser-nephelometry assay for the identification of cerebrospinal fluid." *Neurosurgery*, 50(3): 571-577.
Carter and Cary (2007) "Lateral flow microarrays: a novel platform for rapid nucleic acid detection based on miniaturized lateral flow chromatography," *Nucleic Acids Research* 35(10): e74 (11 pages).
Center for Disease Control and Prevention. Diagnostic Tests for Zika Virus. "Updated Guidance for US Laboratories Testing for Zika Virus Infection Jul. 24, 2017"; Availabe at: https://www.cdc.gov/zika/transmission/index.html, 16 pages.
Chiu et al. (2014) "Biomarker concentration and detection directly on paper," abstract, *MicroTAS Annual Meeting*, San Antonio, Texas, 3 pages.
Chiu et al. (2014) "Dextran-coated gold nanoprobes for the concentration and detection of protein biomarkers," *Annals of Biomedical Engineering* 42(11): 2322-2332.
Chiu et al. (2014) "Manipulating gold nanoparticles to achieve effective and rapid detection of protein biomarkers for resource-poor settings," slides from presentation, not published/distributed. *The Annual UC System wide Bioengineering Symposium*, Irvine, California, 24 slides.
Chiu et al. (2014) "Polymer-coated gold nanoprobes for the concentration and detection of protein biomarkers for resource-poor settings," *The Biomedical Engineering Society Annual Meeting*, San Antonio, Texas, poster, 1 page.
Chiu et al. (2014) "Polymer-coated gold nanoprobes for the concentration and detection of protein biomarkers for resource-poor settings," *The Biomedical Engineering Society Annual Meeting*, San Antonio, Texas, published abstract, 1 page.
Chiu et al. (2014) "Simultaneous concentration and detection of biomarkers on paper," *Lab Chip* 14: 3021-3028.
Chiu et al. (2014) "Simultaneous concentration and detection of biomarkers on paper," poster presentation, *MicroTAS Annual Meeting*, San Antonio, Texas, 1 page.
Chiu et al. (2014) "Simultaneously concentrating and detecting biomarkers on paper," abstract of podium presentation, *The Biomedical Engineering Society Annual Meeting*, San Antonio, Texas, 1 page.
Chiu et al. (2014) "Simultaneously concentrating and detecting biomarkers on paper," slides from podium presentation, *The Biomedical Engineering Society Annual Meeting*, San Antonio, Texas, 52 slides.
Chiu et al. (2015) "Creating the gold standard point-of-care test for sexually transmitted infections," 20 slide deck, not published, not distributed, for judging only, *OneStart Competition*, 20 pages.
Chiu et al. (2015) "Creating the gold standard point-of-care test for sexually transmitted infections," 3 minute/3 slide deck, *OneStart Competition*, 3 pages.
Chiu et al., (2015) "An aqueous two-phase system for the concentration and extraction of proteins from the interface for detection using the lateral-flow immunoassay," *PLoS One* 10: e0142654 (14 pages).
Chiu, et al. (2010) "Generation of Porous Poly(Ethylene Glycol) Hydrogels by Salt Leaching." *Tissue Engineering Part C: Methods* 16: 905-912.
Cho, et al. (2013) "Lateral-flow enzyme immunoconcentration for rapid detection of Listeria monocytogenes." *Anal Bioanal Chem* 405:3313-3319.
Fang et al. (2011) "Barcode lateral flow immunochromatographic strip for prostate acid phosphatase determination," *J. Pharmaceut. Biomed. Anal.*, 56(5): 1035-1040.
Fu et al. (2011) "Enhanced sensitivity of lateral flow tests using a two-dimensional paper network format," *Anal. Chem.* 83(20): 7941-7946 (NIH Public Access—Author Manuscript—12 pages).
Fung et al. (2009) "Development of a creatinine enzyme-based bar-code-style lateral-flow assay," *Analytical and Bioanalytical Chemistry*, 393(4): 1281-1287.

(56) References Cited

OTHER PUBLICATIONS

Fung et al. (2009) "Development of enzyme-based bar code-style lateral-flow assay for hydrogen peroxide determination," *Anal Chim Acta.* 634(1): 89-95.
GCA Saliva-Check Mutans product sheet. 2011. http://www.gcamerica.com/storage/dps_c/GCA_SALIVA-CHECK_MUTANS-iPad.pdf retrieved Sep. 21, 2019.
Jue et al. (2014) "Simultaneous Concentration and Detection of Biomarkers on Paper," published document for the Capstone Design team, *MicroTAS Annual Meeting*, San Antonio, Texas, 7 pages.
Jue et al. (2014) "Using an aqueous two-phase polymer-salt system to rapidly concentrate viruses for improving the detection limit of the lateral-flow immunoassay," *Biotechnology and Bioengineering* 111(12): 2499-2507.
Jue et al. "Simultaneous Concentration and Detection of Biomarkers on Paper," document submitted but not published, UCLA, 23 pages.
Kim, et al. (2013) "Image Analysis of a Lateral Flow Strip Sensor for the Detection of *Escherichia coli* 0157:H7." *J. of Biosystems Eng.* 38(4):335-340.
Leung et al. (2008) "InfectCheck CRP barcode-style lateral flow assay for semi-quantitative detection of C-reactive protein in distinguishing between bacterial and viral infections," *J Immunol Meth.* 336(1): 30-36.
Luo, et al. (2005) "PDMS microfludic device for optical detection of protein immunoassay using gold nanoparticles." *Lab on a Chip* 5:726-729.
Mashayekhi et al. (2009) "Concentration of mammalian genomic DNA using two-phase aqueous micellar systems," *Biotechnology and Bioengineering* 102(6): 1613-1623, publ online Nov. 3, 2008, publ in journal Apr. 15, 2009.
Mashayekhi et al. (2010) "Enhancing the lateral-flow immunoassay for viral detection using an aqueous two-phase micellar system," *Anal. Bioanal. Chem.* 398(7): 2955-2961.
Mashayekhi et al. (2012) "Enhancing the lateral-flow immunoassay for detection of proteins using an aqueous two-phase micellar system," *Anal. Bioanal. Chem.* 404: 2057-2066.
McCudden et al. (2012) "Evaluation of high resolution gel beta 2-transferrin for detection of cerebrospinal fluid leak," *Clinical Chemistry and Laboratory Medicine* 6 pages [ Abastract].
McCudden et al. (2013) "Evaluation of high resolution gel β2-transferrin for detection of cerebrospinal fluid leak." *Clin. Chem. Lab. Med.*, 51(2): 311-315, CCLM / FESCC. 0. 1-5. 10.1515/cclm-2012-0408.
NIH Small Business Technology Transfer Grant Application, Proposal to improve healthcare of tooth decay by developing a point-of-care (POC) diagnostic device, 6 pages, submitted Nov. 19, 2014.
Pereira et al. (2014) "Enhancing the phase separation behavior of a micellar aqueous two-phase system in a paper-based diagnostic," *The Annual UC System wide Bioengineering Symposium*, Irvine, California, poster, 1 page.
Pereira et al. (2014) "Enhancing the phase separation behavior of a micellar aqueous two-phase system in a paper-based diagnostic," *UC Bioengineering Symposium 2014*, Abstract, 2 pages.
Pereira et al. (2014) "Paper-based diagnostic accelerates phase separation of a micellar aqueous two-phase system," *The Biomedical Engineering Society Annual Meeting*, San Antonio, Texas, poster, 1 page.
Pereira et al. (2015) "Improving malaria biomarker detection and accelerating micellar two-phase separation with a paper-based diagnostic," *Department of Engineering, UCLA 90095, UCLA Tech Forum*, abstract, 1 page.
Pereira et al. (2015) "Improving malaria biomarker detection and accelerating micellar two-phase separation with a paper-based diagnostic," *The UCLA Engineering Tech Forum*, Los Angeles, California, poster, 1 page.
Pereira et al. (2015) "Single-step, paper-based concentration and detection of a malaria biomarker," *Analytica Chimica Acta* 882: 83-89.
Pereira et al. "Paper-based diagnostic accelerates phase separation of a micellar aqueous two-phase system," *Department of Engineering, University of California*, Los Angeles, abstract, 2 pages.
Phase Diagnostics, Business Plan, *OneStart Competition* 2015, May 2015, 12 pages.
Sampaio et al. (2009) "Predictability of quantification of beta-trace protein for diagnosis of cerebrospinal fluid leak: Cutoff determination in nasal fluids with two control groups." *Am. J. Rhinol. Allerg.* 23(6): 585-590.
Song, et al. (2016) "Instrument-Free Point-of-Care Molecular Detection of Zika Virus." *Analytical Chemistry* 88: 7289-7294.
Wong et al. (2015) "Direct Reading of Bona Fide Barcode Assays for Diagnostics with Smartphone Apps," *Scientific Reports* 5, Article No. 11727 (11 pages).
Wu et al. (Jul. 21, 2014) "Research highlights: increasing paper possibilities" *Lab on a Chip*, 14(17) 3258-3261.
Yu, et al. (2009) "Flow-through functionalized PDMS microfluidic channels with dextran derivative for ELISAs." *Lab on a Chip* 9:1243-1247.
AU Examination report No. 1 dated May 24, 2021 issued in AU 2020201579.
AU Office Action dated Nov. 4, 2021 issued in AU 2016318103.
CN Third Office Action dated Jun. 22, 2021 issued in CN 201680059385.6.
JP 2nd Office Action dated Aug. 30, 2021 issued in JP 2018-511707.
EP 2nd Office Action dated Jul. 27, 2021 issued in EP 17810966.6.
JP Office Action dated May 17, 2021 issued in JP 2018-564267.
KR Office Action dated Aug. 23, 2021 issued in KR 10-2019-7000413.
U.S. Final Office Action dated Jun. 1, 2021 issued in U.S. Appl. No. 15/756,542.
U.S. Office Action Advisory Action dated Aug. 20, 2021 issued in U.S. Appl. No. 15/756,542.
U.S. Office Action Advisory Action (second) dated Sep. 17, 2021 issued in U.S. Appl. No. 15/756,542.
U.S. Notice of Allowance dated Nov. 16, 2021 issued in U.S. Appl. No. 15/756,542.
U.S. Office Action dated Jun. 4, 2021 issued in U.S. Appl. No. 16/326,687.
U.S. Final Office Action dated May 17, 2021 issued in U.S. Appl. No. 16/498,312.
U.S. Notice of Allowance dated Aug. 23, 2021 issued in U.S. Appl. No. 16/498,312.
AU Office Action dated Oct. 10, 2022, in Application No. AU2016318103.
CA Office Action dated May 19, 2022, in Application No. CA3002020.
CN Fourth Office Action dated Mar. 24, 2022 issued in CN 201680059385.6 with English translation.
CN Office Action dated Aug. 29, 2022 in Application No. CN201780046652 with English translation.
CN Office Action dated Feb. 24, 2022, in Application No. CN201780046652 with English translation.
International Search Report and Written Opinion dated Nov. 30, 2021, in PCT Application No. PCT/US2021/046166.
JP Office Action dated Aug. 8, 2022, in Application No. JP2021-15690 with English translation.
JP Office Action dated Feb. 14, 2022, in Application No. JP2021-15690 with English translation.
JP Office Action dated Mar. 7, 2022, in Application No. JP2018-564267 with English translation.
KR Office Action dated Jan. 25, 2022, in Application No. KR1020167027705 with English translation.
KR Office Action dated Jun. 21, 2022, in Application No. KR10-2019-7000413 with English translation.
Raja, S. et al., "Aqueous Two Phase Systems for the Recovery of Biomolecules—A Review", Science and Technology, 2011, vol. 1, No. 1, pp. 7-16.
Sarangi, B.K. et al., "Purification of Alkaline Protease from Chicken Intestine by Aqueous Two Phase System of Polyethylene Glycol and Sodium Citrate", Journal of Food Science and Technology, Nov. 1, 2010, vol. 48, No. 1, pp. 36-44.
U.S. Non-Final Office Action dated Jun. 24, 2022, in U.S. Appl. No. 16/616,923.

(56) References Cited

OTHER PUBLICATIONS

U.S. Non-Final Office Action dated May 25, 2022, in U.S. Appl. No. 16/751,114.
U.S. Notice of Allowance dated Jan. 12, 2022, in U.S. Appl. No. 16/326,687.
U.S. Restriction Requirement dated Jan. 25, 2022, in U.S. Appl. No. 16/616,923.

BIOMARKER CONCENTRATION AND SIGNAL AMPLIFICATION FOR USE IN PAPER-BASED IMMUNOASSAYS AND A SINGLE PLATFORM FOR EXTRACTING, CONCENTRATING, AND AMPLIFYING DNA

CROSS-REFERENCE TO RELATED APPLICATIONS

This application is a U.S. 371 National Phase of PCT/US2017/036418, filed on Jun. 7, 2017, which claims benefit of and priority to U.S. Ser. No. 62/348,038, filed Jun. 9, 2016, both of which are incorporated herein by reference in their entirety for all purposes.

STATEMENT OF GOVERNMENTAL SUPPORT

[Not Applicable]

BACKGROUND

Assays have been used to detect the presence or the concentration of various substances or pathogens in biological fluids. In a solid phase immunoassay, a receptor, typically an antibody which is specific for the ligand to be detected, is immobilized on a solid support. A test fluid that may comprise the analyte to be detected is contacted with the solid support and a receptor-analyte pair is formed when the target analyte is present. In order to make the receptor-ligand pair visible, labeled antibodies may be used that bind to the receptor-ligand pair followed by visual detection of the labeled antibody bound to the receptor-ligand pair.

The most commercialized point-of-care diagnostic device is the lateral-flow immunoassay (LFA), due to its low cost and simplicity. In typical so-called lateral flow assays, a fluid potentially containing the analyte to be detected is applied to one end of a porous membrane layer and flows in lateral direction through the membrane under the action of capillary forces to be captured by an immobilized "receptor" that is capable of binding the analyte to be detected. LFAs often incorporate a so-called sandwich immunoassay, in which the analyte is sandwiched between a labeled antibody and an antibody immobilized on a solid support.

The LFA, however, suffers from an inferior sensitivity when compared to laboratory-based assays, such as ELISA. While there has been significant effort put forth to improve LFA sensitivity, many of these approaches have relied on the use of expensive, electronic readers or required multiple user steps which detract from the point-of-care nature of the LFA.

Similarly, while efforts have been made to design point-of-care friendly nucleic acid amplification tests (NAATs) for DNA detection, these often either lack sensitivity due to over-simplification, or sacrifice ease-of-use to retain test accuracy. Moreover, current point-of-care (POC) NAATs still typically require equipment to analyze and process samples. Thus, there are no commercialized POC NAATs that are entirely stand-alone or portable.

SUMMARY

Various embodiments contemplated herein may include, but need not be limited to, one or more of the following:

Embodiment 1

A device for the detection and/or quantification of an analyte in a sample, said device comprising:
 an aqueous two-phase system (ATPS) comprising a mixed phase solution that separates into a first phase solution and a second phase where, in use, said first phase solution becomes a leading phase and said second phase solution becomes a lagging phase;
 a lateral-flow assay (LFA) or a flow-through assay; and
 a probe and/or a development reagent, where in use, said probe associates with said first phase solution in said leading phase of said ATPS and/or said development reagent associates with said second phase solution in said lagging phase of said ATPS.

Embodiment 2

The device of embodiment 1, wherein the LFA comprises a porous matrix that is configured to receive and/or contain said ATPS or components thereof and/or said probe, and/or said development reagent.

Embodiment 3

The device according to any one of embodiments 1-2, wherein said LFA comprises a conjugate pad, a test line comprising an antibody that binds said analyte, optionally a control line comprising a secondary antibody, optionally an absorbent pad, and optionally a sample pad.

Embodiment 4

A device for the detection and/or quantification of an analyte in a sample, said device comprising:
 a flow-through system comprising:
  a concentration component comprising an aqueous two phase system (ATPS) comprising a mixed phase solution where, in use, said first phase solution becomes a leading phase and said second phase solution becomes a lagging phase;
  a probe and/or a development reagent where, in use, said probe associates with said first phase solution in said leading phase of said ATPS and/or said development reagent associates with said second phase solution in said lagging phase of said ATPS; and
  a detection component disposed beneath said concentration component.

Embodiment 5

The device of embodiment 4, wherein said concentration component comprises one or more layers of a paper.

Embodiment 6

The device according to any one of embodiments 4-5, wherein said detection component comprises a conjugate pad, a reaction pad, and optionally a sink.

Embodiment 7

The device according to any one of embodiments 1-6, wherein said probe is disposed in said ATPS.

Embodiment 8

The device of embodiment 7, wherein said probe is associated with said first phase solution of said ATPS.

Embodiment 9

The device according to any one of embodiments 1-8, wherein said development reagent is disposed in said ATPS.

Embodiment 10

The device of embodiment 9, wherein said development reagent is associated with said second phase solution of said ATPS.

Embodiment 11

The device according to any one of embodiments 1-10, wherein said device is configured for said ATPS to be combined with said sample before application to said device.

Embodiment 12

The device according to any one of embodiments 1-11, wherein said ATPS is dehydrated on the lateral flow assay or in a concentration component of a flow-through assay before the device is contacted with the sample.

Embodiment 13

The device of embodiment 12, wherein said probe is dehydrated on the lateral-flow assay or in a concentration component of a flow-through assay before the device is contacted with the sample.

Embodiment 14

The device according to any one of embodiments 12-13, wherein said development reagent is dehydrated on the lateral-flow assay or in a concentration component of a flow-through assay before the device is contacted with the sample.

Embodiment 15

The device according to any one of embodiments 12-14, wherein the ATPS comprises a mixed phase solution that separates into a first phase solution and a second phase solution after the device is contacted with the sample.

Embodiment 16

The device according to any one of embodiments 1-15, wherein said probe is selected to extremely partition into a hydrophilic phase of said ATPS.

Embodiment 17

The device according to any one of embodiments 1-15, wherein said probe is selected to extremely partition into a hydropobic phase of said ATPS.

Embodiment 18

The device according to any one of embodiments 1-17, wherein said development reagent is selected to extremely partition into a hydrophobic phase of said ATPS.

Embodiment 19

The device according to any one of embodiments 1-17, wherein said development reagent is selected to extremely partition into a hydrophilic phase of said ATPS.

Embodiment 20

The device according to any one of embodiments 1-19, wherein said ATPS is selected from the group consisting of a polymer/salt ATPS, a polymer/polymer ATPS, a micellar/polymer ATPS, and a micellar ATPS.

Embodiment 21

The device of embodiment 20, wherein said wherein a first phase solution of said ATPS comprises a Component 1 of Table 1.

Embodiment 22

The device of embodiment 20, wherein said wherein a second phase solution of said ATPS comprises a Component 2 of Table 1.

Embodiment 23

The device of embodiment 20, wherein said wherein a first phase solution of said ATPS comprises a Component 1 of Table 1 and a second phase solution of said ATPS comprises a Component 2 of Table 1.

Embodiment 24

The device of embodiment 20, wherein said ATPS is a polymer/salt ATPS.

Embodiment 25

The device of embodiment 24, wherein said ATPS is a PEG/salt ATPS.

Embodiment 26

The device according to any one of embodiments 24-25, wherein said probe partitions into a salt-rich phase of said polymer/salt ATPS and said development reagent partitions into a polymer-rich phase of said polymer/salt ATPS.

Embodiment 27

The device of embodiment 20, wherein said ATPS is a micellar ATPS.

Embodiment 28

The device of embodiment 27, wherein said sad probe partitions into a micellar-poor phase of said ATPS and said development reagent partitions into a micellar-rich phase of said ATPS.

Embodiment 29

The device according to any one of embodiments 1-28, wherein said probe comprises a binding moiety that binds to said target analyte.

Embodiment 30

The device of embodiment 29, wherein said target analyte comprises a moiety selected from the group consisting of a protein, a nucleic acid, a sugar or lectin, and a microorganism.

Embodiment 31

The device of embodiment 30, wherein said target analyte comprises a microorganism selected from the group consisting of a bacterium, a protozoan, a fungus, a virus, and an alga.

Embodiment 32

The device of embodiment 30, wherein said target analyte comprises a biomarker for a microorganism.

Embodiment 33

The device of embodiment 32, wherein said target analyte comprises a biomarker for a microorganism selected from the group consisting of a bacterium, a protozoan, a fungus, a virus, and an alga.

Embodiment 34

The device of embodiment 32, wherein said target analyte comprises a biomarker for a disease condition, a biomarker for food safety (or hazard), or a biomarker for a bioterror agent.

Embodiment 35

The method according to any one of embodiments 29-34, wherein said binding moiety is selected from the group consisting of an antibody or antibody fragment, a lectin, a nucleic acid, and an aptamer.

Embodiment 36

The device of embodiment 35, wherein said probe comprises an antibody or an antibody fragment.

Embodiment 37

The device according to any one of embodiments 1-36, wherein said probe comprises a material selected from the group consisting of a synthetic polymer, a metal, a mineral, a glass, a quartz, a ceramic, a biological polymer, and a plastic.

Embodiment 38

The device of embodiment 37, wherein said probe comprises a material selected from the group consisting of polyethylene, polypropylene, cellulose, chitin, nylon, polyoxymethylene, polytetrafluoroethylene, or polyvinyl chloride, dextran, polypropylene, or polyethylene glycol.

Embodiment 39

The device of embodiment 37, wherein said probe comprises a metal selected from the group consisting of gold, silver, iron, platinum, palladium, cerium, and titanium.

Embodiment 40

The device according to any one of embodiments 1-39, wherein said probe comprises a nanoparticle.

Embodiment 41

The device according to any one of embodiments 1-40, wherein said probe comprises an agent that can react with said development reagent to produce a detectable signal.

Embodiment 42

The device of embodiment 41, wherein said agent comprises an enzyme that reacts with a substrate to form a strong visible signal.

Embodiment 43

The device of embodiment 42, wherein said development reagent comprises said substrate.

Embodiment 44

The device of embodiment 42, wherein said development reagent comprises an antibody that binds said enzyme.

Embodiment 45

The device of embodiment 41, wherein said agent comprises a substrate that reacts with an enzyme to form a strong visible product.

Embodiment 46

The device of embodiment 45, wherein said development reagent comprises said enzyme.

Embodiment 47

The device according to any one of embodiments 42 and 46, wherein said enzyme is selected from the group consisting of alkaline phosphatase, horse radish (or other) peroxidase, and glucose oxidase.

Embodiment 48

The device according to any one of embodiments 1-47, wherein said probe comprises a coating that has an affinity for the first phase solution or the second phase solution of said ATPS.

Embodiment 49

The device of embodiment 48, wherein said coating comprises a material selected from the group consisting of polypropylene glycol, polyethylene glycol, dextran, a hydrophilic protein, and a hydrophobic protein.

Embodiment 50

The device according to any one of embodiments 1-49, wherein said device comprises two or more probes that each interact with different analytes.

Embodiment 51

The device of embodiment 50, wherein said device includes at least two different probes, or at least 3 different probes, or at least 4 different probes, or at least 5 different probes, or at least 7 different probes, or at least 10 different probes, or at least 15 different probes, or at least 20 different probes.

Embodiment 52

The device according to any one of embodiments 1-51, wherein said device is configured to perform a sandwich assay.

Embodiment 53

An aqueous two phase system (ATPS) comprising:
a mixed phase solution that separates into a first phase solution and a second phase where, in use in an LFA or other porous medium, said first phase solution becomes a leading phase and said second phase solution becomes a lagging phase; and
a probe and/or a development reagent, said probe associates with said first phase solution and said development reagent associates with said second phase solution.

Embodiment 54

The aqueous two phase system of embodiment 53, wherein said ATPS is selected from the group consisting of a polymer/salt ATPS, a polymer/polymer ATPS, a micellar/polymer ATPS, and a micellar ATPS.

Embodiment 55

The aqueous two phase system of embodiment 54, wherein said wherein a first phase of solution of said ATPS comprises a Component 1 of Table 1 and a second phase solution of said ATPS comprises a Component 2 of Table 1.

Embodiment 56

The aqueous two phase system of embodiment 54, wherein said ATPS is a polymer/salt ATPS.

Embodiment 57

The aqueous two phase system of embodiment 56, wherein said ATPS is a PEG/salt ATPS.

Embodiment 58

The aqueous two phase system according to any one of embodiments 56-57, wherein said probe partitions into a salt-rich phase of said polymer/salt ATPS and said development reagent partitions into a polymer-rich phase of said polymer/salt ATPS.

Embodiment 59

The aqueous two phase system of embodiment 54, wherein said ATPS is a micellar ATPS.

Embodiment 60

The aqueous two phase system of embodiment 59, wherein said probe partitions into a micellar-poor phase of said ATPS and said development reagent partitions into a micellar-rich phase of said ATPS.

Embodiment 61

The aqueous two phase system according to any one of embodiments 1-60, wherein said probe comprises a binding moiety that binds to said target analyte.

Embodiment 62

The aqueous two phase system according to any one of embodiments 1-61, wherein said ATPS is disposed in a porous medium.

Embodiment 63

The aqueous two phase system according to any one of embodiments 1-61, wherein said ATPS is disposed in a paper.

Embodiment 64

The aqueous two phase system according to any one of embodiments 1-61, wherein said ATPS is disposed in a lateral flow assay (LFA).

Embodiment 65

The aqueous two phase system according to any one of embodiments 1-61, wherein said ATPS is disposed in a flow-through system.

Embodiment 66

A method of detecting and/or quantifying an analyte, said method comprising:
applying a sample to an aqueous two phase system (ATPS) to concentrate said analyte, if present in said sample, into one phase of the ATPS to provide an analyte containing phase;
applying the analyte containing phase to a lateral-flow assay (LFA) or flow-through assay in which a detection probe binds to said analyte in said LFA or flow-through assay;
applying a development reagent to said LFA or flow-through assay to enhance a signal produced by said detection probe; and
detecting and/or quantifying said signal to indicate the presence and/or quantity of said analyte in said sample.

Embodiment 67

The method of embodiment 66, wherein said lateral-flow assay or flow-through assay is a lateral-flow assay.

Embodiment 68

The method of embodiment 66, wherein said lateral-flow assay or flow-through assay is a flow-through assay.

Embodiment 69

The method according to any one of embodiments 66-68, wherein said ATPS is applied to a paper and phase separates as said ATPS flows through said paper providing a "concentrate-as-it-flows" ATPS.

Embodiment 70

The method of embodiment 69, wherein said ATPS produces a leading more hydrophobic phase and a lagging more hydrophilic phase when applied to a paper.

Embodiment 71

The method of embodiment 69, wherein said ATPS produces a leading more hydrophilic phase and a lagging more hydrophobic phase when applied to a paper.

Embodiment 72

The method according to any one of embodiments 66-71, wherein said LFA or flow-through assay is one in which a binding moiety captures said analyte and in which said detection probe binds to said captured analyte.

Embodiment 73

The method according to any one of embodiments 66-72, wherein said analyte containing phase is manually or robotically removed from said ATPS and then applied to said lateral-flow assay.

Embodiment 74

The method of embodiment 73, wherein said detection probe is provided as component of said LFA or flow-through assay.

Embodiment 75

The method according to any one of embodiments 73-74, wherein said development reagent is then applied to said lateral-flow assay independently from said ATPS.

Embodiment 76

The method according to any one of embodiments 66-72, wherein said probe and said development reagent are both applied to, or provided in, said ATPS and said components of said ATPS are selected to substantially partition said probe into a first phase of said ATPS and said development reagent into a second phase of said ATPS.

Embodiment 77

The method of embodiment 76, wherein said ATPS forms a leading phase and a lagging phase when applied to a paper substrate and said leading phase delivers said concentrated analyte and said probe to an LFA test strip or flow-through assay, followed by a said lagging phase that later delivers said development reagent to said test strip or flow-through assay.

Embodiment 78

The method according to any one of embodiments 76-77, wherein said probe is selected to extremely partition into a hydrophilic phase of said ATPS.

Embodiment 79

The method according to any one of embodiments 76-77, wherein said probe is selected to extremely partition into a hydrophobic phase of said ATPS.

Embodiment 80

The method according to any one of embodiments 76-79, wherein said development reagent is selected to extremely partition into a hydrophobic phase of said ATPS.

Embodiment 81

The method according to any one of embodiments 76-79, wherein said development reagent is selected to extremely partition into a hydrophylic phase of said ATPS.

Embodiment 82

The method according to any one of embodiments 66-81, wherein said ATPS is selected from the group consisting of a polymer/salt ATPS, a polymer/polymer ATPS, a micellar/polymer ATPS, and a micellar ATPS.

Embodiment 83

The method of embodiment 82, wherein said first phase of solution of said ATPS comprises a Component 1 of Table 1 and a second phase solution of said ATPS comprises a Component 2 of Table 1.

Embodiment 84

The method of embodiment 82, wherein said ATPS is a polymer/salt ATPS.

Embodiment 85

The method of embodiment 84, wherein said ATPS is a PEG/salt ATPS.

Embodiment 86

The method according to any one of embodiments 84-85, wherein said probe partitions into a salt-rich phase of said polymer/salt ATPS and said development reagent partitions into a polymer-rich phase of said polymer/salt ATPS.

Embodiment 87

The method of embodiment 82, wherein said ATPS is a micellar ATPS.

Embodiment 88

The method of embodiment 87, wherein said sad probe partitions into a micellar-poor phase of said ATPS and said development reagent partitions into a micellar-rich phase of said ATPS.

Embodiment 89

The method according to any one of embodiments 66-88, wherein said probe comprises a binding moiety that binds to said target analyte.

Embodiment 90

The method of embodiment 89, wherein said target analyte comprises a moiety selected from the group consisting of a protein, a nucleic acid, a sugar or lectin, and a microorganism.

Embodiment 91

The method of embodiment 90, wherein said target analyte comprises a microorganism selected from the group consisting of a bacterium, a protozoan, a fungus, a virus, and an alga.

Embodiment 92

The method of embodiment 90, wherein said target analyte comprises a biomarker for a microorganism.

Embodiment 93

The method of embodiment 92, wherein said target analyte comprises a biomarker for a microorganism selected from the group consisting of a bacterium, a protozoan, a fungus, a virus, and an alga.

Embodiment 94

The method according to any one of embodiments 89-92, wherein said binding moiety is selected from the group consisting of an antibody or antibody fragment, a lectin, a nucleic acid, and an aptamer.

Embodiment 95

The method of embodiment 94, wherein said probe comprises an antibody or an antibody fragment.

Embodiment 96

The method according to any one of embodiments 66-95, wherein said probe comprises a material selected from the group consisting of a synthetic polymer, a metal, a mineral, a glass, a quartz, a ceramic, a biological polymer, and a plastic.

Embodiment 97

The method of embodiment 96, wherein said probe comprises a material selected from the group consisting of polyethylene, polypropylene, cellulose, chitin, nylon, polyoxymethylene, polytetrafluoroethylene, or polyvinyl chloride, dextran, polypropylene, or polyethylene glycol.

Embodiment 98

The method of embodiment 96, wherein said probe comprises a metal selected from the group consisting of gold, silver, iron, platinum, palladium, cerium, and titanium.

Embodiment 99

The device according to any one of embodiments 66-98, wherein said probe comprises a nanoparticle.

Embodiment 100

The method according to any one of embodiments 66-99, wherein said probe comprises an agent that can react with said development reagent to produce a detectable signal.

Embodiment 101

The method of embodiment 100, wherein said agent comprises an enzyme that reacts with a substrate to form a strong visible signal.

Embodiment 102

The method of embodiment 101, wherein said development reagent comprises said substrate.

Embodiment 103

The method of embodiment 101, wherein said development reagent comprises an antibody that binds said enzyme.

Embodiment 104

The method of embodiment 100, wherein said agent comprises a substrate that reacts with an enzyme to form a strong visible product.

Embodiment 105

The method of embodiment 104, wherein said development reagent comprises said enzyme.

Embodiment 106

The method according to any one of embodiments 101 and 105, wherein said enzyme is selected from the group consisting of alkaline phosphatase, horse radish (or other) peroxidase, and glucose oxidase.

Embodiment 107

The device according to any one of embodiments 66-106, wherein said probe comprises a coating that has an affinity for the first phase solution or the second phase solution of said ATPS.

Embodiment 108

The device of embodiment 107, wherein said coating comprises a material selected from the group consisting of polypropylene glycol, polyethylene glycol, dextran, a hydrophilic protein, and a hydrophobic protein.

Embodiment 109

The method according to any one of embodiments 66-108, wherein said method is performed using a device according to any one of embodiments 1-52.

Embodiment 110

A kit for the detection and/or quantification of an analyte, said kit comprising: a device according to any one of embodiments 1-52; and a collection device for collecting a sample.

Embodiment 111

The kit of embodiment 110, wherein said collection device comprises a device for collecting oral fluid.

Embodiment 112

The kit of embodiment 110, wherein said collection device comprises a device for collecting blood.

Embodiment 113

The kit of embodiment 110, wherein said collection device comprises a urine collection device.

Embodiment 114

The kit of embodiment 110, wherein said collection device comprises a device for collecting vaginal fluid or from an endocervical swab.

Embodiment 115

The kit of embodiment 110, wherein said collection device comprises a device for an environmental sample.

Embodiment 116

A method of purifying and amplifying a nucleic acid, said method comprising: providing an aqueous two-phase system (ATPS) comprising a mixed phase solution that separates into a first phase solution and a second phase solution where said ATPS is one in which a nucleic acid will partition into either the first phase solution or the second phase solution or said ATPS is one in which a nucleic acid will localizes into the interface between said first phase solution and said second phase solution; introducing a sample comprising a nucleic acid into said ATPS, wherein said nucleic acid partitions into said first phase solution or said second phase solution or said interface between said first phase solution and said second phase solution to provide a concentrated nucleic acid; and amplifying said concentrated nucleic acid in a nucleic amplification reaction to produce an amplified nucleic acid.

Embodiment 117

The method of embodiment 116, wherein said nucleic acid is a DNA.

Embodiment 118

The method of embodiment 116, wherein said nucleic acid is an RNA.

Embodiment 119

The method of embodiment 116, wherein said nucleic acid is a DNA reverse transcribed from an RNA.

Embodiment 120

The method according to any one of embodiments 116-119, wherein said ATPS is selected from the group consisting of a polymer/salt ATPS, a polymer/polymer ATPS, a micellar/polymer ATPS, and a micellar ATPS.

Embodiment 121

The method of embodiment 120, wherein said wherein a first phase of solution of said ATPS comprises a Component 1 of Table 1 and a second phase solution of said ATPS comprises a Component 2 of Table 1.

Embodiment 122

The method according to any one of embodiments 116-121, wherein said amplifying comprises: recovering said concentrated nucleic acid from said first phase, method comprises recovering said nucleic acid from said first phase solution or said second phase solution or said interface between said first phase solution and said second phase solution to provide recovered concentrated nucleic acid; and introducing said recovered concentrated nucleic acid into a nucleic acid amplification reaction to amplify said nuclei acid.

Embodiment 123

The method of embodiment 122, wherein said nucleic acid amplification reaction comprises a polymerase chain reaction (PCR) reaction system.

Embodiment 124

The method of embodiment 122, wherein said nucleic acid amplification reaction comprises an isothermal amplification system.

Embodiment 125

The method of embodiment 124, wherein said nucleic acid amplification reaction comprises an amplification system selected from the group consisting of a Self-Sustained Sequence Reaction (3 SR), a Nucleic acid Based Transcription Assay (NASBA), a Transcription Mediated Amplification (TMA), a Strand Displacement Amplification (SDA), a Helicase-Dependent Amplification (HDA), a Loop-Mediated isothermal amplification (LAMP), stem-loop amplification, signal mediated amplification of RNA technology (SMART), isothermal multiple displacement amplification (IMDA), a single primer isothermal amplification (SPIA), circular helicase-dependent amplification (cHDA), and a Recombinase Polymerase Amplification (RPA).

Embodiment 126

The method according to any one of embodiments 116-121, wherein said amplifying comprises combining reagents for isothermal nucleic acid amplification with said ATPS.

Embodiment 127

The method of embodiment 126, wherein said nucleic acid amplification reaction comprises an isothermal amplification system.

Embodiment 128

The method of embodiment 127, wherein said nucleic acid amplification reaction comprises an amplification system selected from the group consisting of a Self-Sustained Sequence Reaction (3 SR), a Nucleic acid Based Transcription Assay (NASBA), a Transcription Mediated Amplification (TMA), a Strand Displacement Amplification (SDA), a Helicase-Dependent Amplification (HDA), a Loop-Mediated isothermal amplification (LAMP), stem-loop amplification, signal mediated amplification of RNA technology (SMART), isothermal multiple displacement amplification (IMDA), a single primer isothermal amplification (SPIA), circular helicase-dependent amplification (cHDA), and a Recombinase Polymerase Amplification (RPA).

Embodiment 129

The method according to any one of embodiments 127-128, wherein said method comprises performing said isothermal amplification at room temperature or at a temperature lower than room temperature.

Embodiment 130

The method according to any one of embodiments 127-128, wherein said method comprises heating said ATPS containing reagents for isothermal amplification to a substantially constant temperature.

Embodiment 131

The method according to any one of embodiments 127-130, wherein said amplification comprises a helicase-dependent amplification and is performed at a constant temperature of about 65° C.

Embodiment 132

The method according to any one of embodiments 126-131, wherein said method is performed in a single vessel.

Embodiment 133

The method according to any one of embodiments 126-131, wherein said method is performed a plurality of nucleic acid samples with a different sample each in a well of a multi-well plate.

Embodiment 134

The method of embodiment 133, wherein said plurality of samples comprises at least 2 samples, or at least 4 samples, or at least 8 samples, or at least 16 samples, or at least 32 samples, or at least 64 samples, or at least 128 samples.

Embodiment 135

The method according to any one of embodiments 126-131, wherein said method is performed in a chamber or channel of a microfluidic system (e.g., lab on a chip).

Embodiment 136

The method according to any one of embodiments 116-135, wherein said sample is a cell lysate.

Embodiment 137

The method according to any one of embodiments 116-135, wherein said sample is a nucleic acid.

Embodiment 138

The method according to any one of embodiments 116-135, wherein said sample comprises intact cells and said ATPS is an ATPS that lyses cells.

Embodiment 139

The method according to any one of embodiments 116-138, wherein said ATPS is a micellar ATPS.

Embodiment 140

The method according to any one of embodiments 116-138, wherein said sample comprises blood or blood spots and said ATPS is one that resolubilizes blood spots.

Embodiment 141

The method of embodiment 140, wherein said ATPS comprises a PEG/Dextran ATPS.

Embodiment 142

The method of embodiment 140, wherein said ATPS comprises a UCON/Dextran ATPS.

Embodiment 143

A kit for purifying and amplifying a nucleic acid, said kit comprising:
   a container containing components of an aqueous two phase system (ATPS); and
   a container containing one or more components of an isothermal nucleic acid amplification system.

Embodiment 144

The kit of embodiment 143, wherein said container containing components of an ATPS and said container containing a component of an isothermal nucleic acid amplification system are the same container.

Embodiment 145

The kit of embodiment 143, wherein said container containing components of an ATPS and said container containing a component of an isothermal nucleic acid amplification system are different containers.

Embodiment 146

The kit according to any one of embodiments 143-145, wherein said container containing one or more components of an isothermal nucleic acid amplification system contains one or more components of a reaction system selected from the group consisting of a Self-Sustained Sequence Reaction (3 SR), a Nucleic acid Based Transcription Assay (NASBA), a Transcription Mediated Amplification (TMA), a Strand Displacement Amplification (SDA), a Helicase-Dependent Amplification (HDA), a Loop-Mediated isothermal amplification (LAMP), stem-loop amplification, signal mediated amplification of RNA technology (SMART), isothermal multiple displacement amplification (IMDA), a single primer isothermal amplification (SPIA), circular helicase-dependent amplification (cHDA), and a Recombinase Polymerase Amplification (RPA).

Embodiment 147

The kit of embodiment 146, wherein said one or more components comprise an enzyme that performs the nucleic acid amplification reaction.

Embodiment 148

The kit of embodiment 146 wherein said one or more components comprises a helicase.

Embodiment 149

The kit according to any one of embodiments 143-148, wherein said ATPS is selected from the group consisting of a polymer/salt ATPS, a polymer/polymer ATPS, a micellar/polymer ATPS, and a micellar ATPS.

Embodiment 150

The kit of embodiment 149, wherein said wherein a first phase of solution of said ATPS comprises a Component 1 of Table 1 and a second phase solution of said ATPS comprises a Component 2 of Table 1.

Embodiment 151

The kit according to any one of embodiments 143-149, wherein said ATPS comprises a micellar ATPS.

Embodiment 152

The kit according to any one of embodiments 143-149, wherein said ATPS comprises a PEG/Dextran ATPS.

Embodiment 153

The kit according to any one of embodiments 143-149, wherein said ATPS comprises a UCON/Dextran ATPS.

Embodiment 154

The kit according to any one of embodiments 143-153, wherein said kit contains instructional materials providing protocols to perform a method according to any one of embodiments 126-142.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The terms "nucleic acid" or "oligonucleotide" or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) *Tetrahedron* 49(10): 1925) and references therein; Letsinger (1970) 1 *Org. Chem.* 35:3800; Sprinzl et al. (1977) *Eur. J. Biochem.* 81: 579; Letsinger et al. (1986) *Nucl. Acids Res.* 14: 3487; Sawai et al. (1984) *Chem. Lett.* 805, Letsinger et al. (1988) *J Am. Chem. Soc.* 110: 4470; and Pauwels et al. (1986) *Chemica Scripta* 26: 141 9), phosphorothioate (Mag et al. (1991) *Nucleic Acids Res.* 19:1437; and U.S. Pat. No. 5,644,048), phosphorodithioate (Briu et al. (1989) *J. Am. Chem. Soc.* 111:2321, O-methylphophoroamidite linkages (see Eckstein, *Oligonucleotides and Analogues: A Practical Approach*, Oxford University Press), and peptide nucleic acid backbones and linkages (see Egholm (1992)*J Am. Chem. Soc.* 114:1895; Meier et al. (1992) *Chem. Int. Ed. Engl.* 31: 1008; Nielsen (1993) *Nature,* 365: 566; Carlsson et al. (1996) *Nature* 380: 207). Other analog nucleic acids include those with positive backbones (Denpcy et al. (1995) *Proc. Natl. Acad. Sci. USA* 92: 6097; non-ionic backbones (U.S. Pat. Nos. 5,386,023, 5,637,684, 5,602,240, 5,216,141 and 4,469,863; Angew. (1991) *Chem. Intl. Ed. English* 30: 423; Letsinger et al. (1988) *J. Am. Chem. Soc.* 110: 4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghui and P. Dan Cook; Mesmaeker et al. (1994), *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, *Carbohydrate Modifications in Antisense Research*, Ed. Y. S. Sanghui and P. Dan Cook. Nucleic acids containing one or more carbocyclic sugars are also included within the definition of nucleic acids (see Jenkins et al. (1995), *Chem. Soc. Rev.* pp 169-1'76). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments. In addition, it is possible that nucleic acids of the present invention can alternatively be triple-stranded.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region thereby converting the $(Fab')_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) *Protein Eng.* 8: 1323-1331).

An aptamer is an antibody-analogue formed from nucleic acids. An aptazyme is an enzyme analogue, formed from nucleic acids. In particular, an aptazyme can function to change configuration to capture a specific molecule, only in the presence of a second, specific, analyte. Aptamers may not even require the binding of the first label to be detected in some assays, such as nano-CHEM-FET, where the reconfiguration would be detected directly.

The term "binding moiety", or a member of a "binding pair" refers to molecules that specifically bind other molecules, cells, microorganisms, and the like to form a binding complex such as antibody-antigen, lectin-carbohydrate, nucleic acid-nucleic acid, biotin-avidin, etc. Such binding moieties include, but are not limited to, monomeric or polymeric nucleic acids, aptamers, aptazymes, proteins, polysaccharides, sugars, lectins, and the like (see, e.g., Haugland, "Handbook of Fluorescent Probes and Research Chemicals" (Sixth Edition)), and any of the molecules capable of forming a binding pair as described above.

The phrase "specifically binds" indicates that the molecule binds preferentially to the target of interest or binds with greater affinity to the target (analyte) than to other molecules. For example, an antibody will selectively bind to the antigen against which it was raised. A DNA molecule will bind to a substantially complementary sequence and not to unrelated sequences under stringent conditions. Specific binding can refer to a binding reaction that is determinative of the presence of a target in a heterogeneous population of molecules (e.g., proteins and other biologics). Thus, under designated conditions (e.g. immunoassay conditions in the case of an antibody or stringent hybridization conditions in the case of a nucleic acid), the specific ligand or antibody binds to its particular "target" molecule and does not bind in a significant amount to other molecules present in the sample.

The term small organic molecules refers to molecules of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

The term analyte refers to any moiety that is to be detected. Analytes include, but are not limited to particular biomolecules (proteins, antibodies, nucleic acids), bacteria or components thereof, viruses or components thereof (e.g., coat proteins), fungi or components thereof, protozoa or components thereof, drugs, toxins, food pathogens, and the like.

The term "paper", as used herein, is not limited to thin sheets from the pulp of wood or other fibrous plant substances although, in certain embodiments the use of such papers in the devices described herein is contemplated. Papers more generally refer to porous materials often in sheet form, but not limited thereto that allow a fluid to flow through.

In some embodiments, the porous matrix is sufficiently porous to allow the mixed phase solution, first phase solution and/or second phase solution of an aqueous two phase system (ATPS), and/or target analyte, to flow through the LFA. In some embodiments, the porous matrix is sufficiently long and/or deep enough for the mixed phase solution, first phase solution and/or second phase solution, and/or target analyte, to flow vertically and/or horizontally through the LFA or spot assay device. In some embodiments, the first phase solution flows through the porous matrix at a first rate and the second phase solution flows through the porous matrix at a second rate, where the first rate and the second rate are different. In some embodiments of the LFA or spot assay the porous matrix comprises inter alia a material such as a scintered glass ceramic, a mineral, cellulose, a fiberglass, a nitrocellulose, polyvinylidene fluoride, a nylon, a charge modified nylon, a polyethersulfone, combinations thereof, and the like.

DETAILED DESCRIPTION

Figure 1:
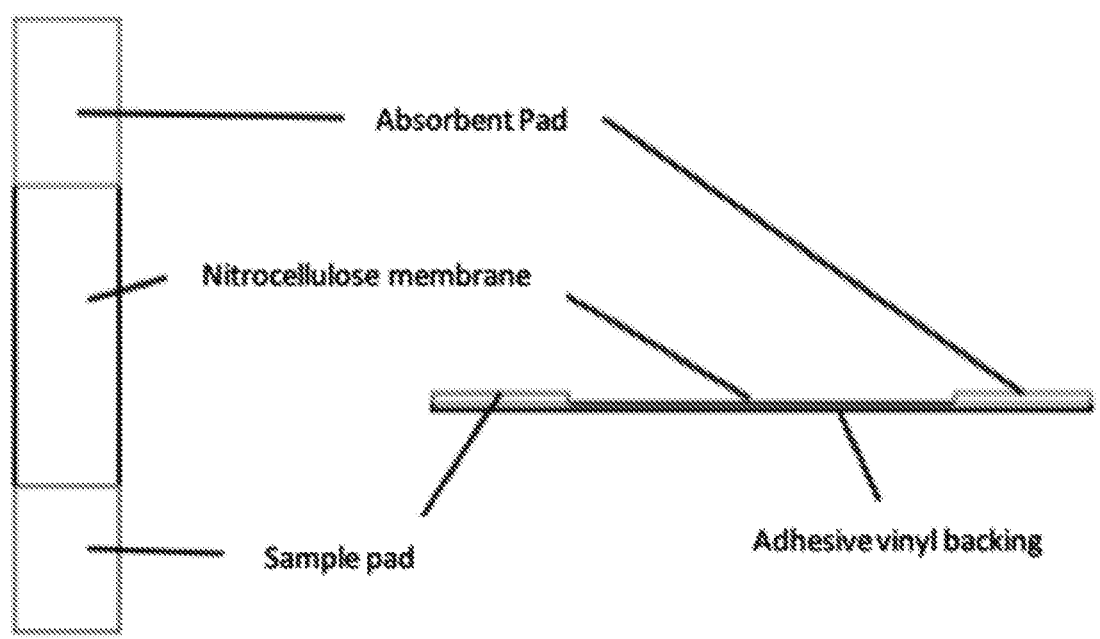
FIG. 1 shows a schematic of a typical lateral-flow immunoassay test strip (top) and the sandwich format of a lateral-flow immunoassay (bottom).
Figure 1:
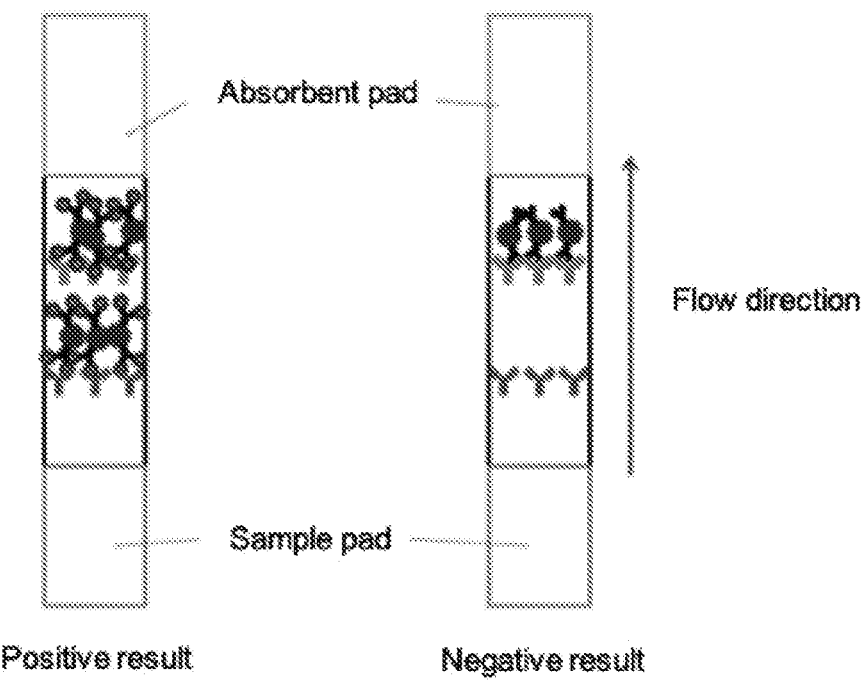

In certain embodiments methods and devices are provided that significantly increase lateral-flow assay sensitivity. In various embodiments LFA (or flow through assay) sensitivity is significantly increased through integration of the aqueous two-phase system (ATPS) and signal enhancement reactions. In certain embodiments the ATPS serves a dual role to concentrate the target biomarker as well as sequentially deliver signal enhancement reagents across the LFA (or flow through assay) detection zone. This novel integration of technologies allows for the improvement of LFA (or flow through assay) sensitivity all while maintaining a single user application step and a low cost device.

In certain embodiments methods and devices are also provided for simple and effective nucleic acid amplification tests (NAATs). In certain embodiments the methods significantly reduce the steps to yield a portable NAAT through combining aqueous two phase systems (ATPSs) with DNA amplification. The final product is a single platform that combines sample preparation and DNA amplification into one step. Despite simplification, these tests have increased sensitivity and accuracy when compared to current NAATs that require multiple complex steps, equipment, and trained personnel to achieve the same outcome. Moreover, with this one-step platform, parameters can be easily tuned to broaden its application for detection of a variety of infectious diseases, making it a truly stand-alone NAAT diagnostic for use in developing countries.

In certain embodiments methods and devices described herein can be provided for analyte collection, extraction, concentration, and detection for clinical applications. In certain embodiments the methods and devices permit the rapid detection and/or quantification of bacteria, fungi, and viruses in biological samples (e.g., oral fluid or tissue sample, urine, blood or blood fraction, cerebrospinal fluid, lymph, tissue biopsies, vaginal samples, and the like), food samples, environmental samples, and the like.

In certain embodiments the assays and devices provided herein are accurate, sensitive, portable, disposable, and well suited to use at point of care, for in field environmental testing, field food testing, and the like, with minimal training or equipment.

Methods and Devices that Increase LFA (or Flow Through Assay) Sensitivity.

In various embodiments the concentrating capabilities of the ATPS can be used in conjunction with the LFA (or flow through assay) to achieve significant (e.g., 10-100 fold or grater) improvements in LFA (or flow through assay) detection limit, approaching the sensitivity of lab-based assays such as the enzyme-linked immunosorbent assay (ELISA) (see, e.g., PCT Publication No: WO 2015/134938 (PCT/US2015/019297), and copending application U.S. Ser. No. 62/214,801, filed on Sep. 4, 2015, which are both incorporated herein by reference for the methods and devices disclosed therein. To use the ATPS for analyte concentration, the sample of interest is typically applied to the ATPS where the added analytes distribute, or partition, between the two aqueous phases based on various physical and chemical properties, such as size and hydrophilicity. Analytes that partition extremely into one of the two phases can be concentrated in that phase by severely decreasing its volume. The aqueous nature of the system can also provide a mild environment for biomolecules, stabilizing their structure and biological activities.

It is common for many proteins to partition rather evenly between the two phases of an ATPS, resulting in a poor concentrating ability. In order to enhance the ability of the ATPS to concentrate proteins (or other analytes), various probes (e.g., gold nanoprobes (GNPs) coated with antibodies specific to the target of interest), that can capture the target protein (or other analyte), drive them into the desired phase for concentration, and can, optionally, serve as a colorimetric indicator for LFA can be utilized. Additionally, ATPS separation on paper, provides a method that can greatly enhance and accelerate the phase separation process. When a well-mixed ATPS solution is applied to a porous, paper, it can separate into its respective phases as it flows through the paper, with the less viscous phase being the leading phase, and the more viscous phase being the lagging phase. For a PEG-salt ATPS system, this corresponds to a leading salt-rich phase and a lagging PEG-rich phase. Additionally, the use of a 3-D paper wick results in the further enhancement of ATPS separation on paper. By placing an LFA strip downstream of the 3-D wick, we have seamlessly integrated the concentration and detection steps into one device.

A typical LFA consists of at least three components: a sample pad where the sample is applied to the test strip, a detection zone where there is binding and where results can be observed, and an absorbent pad which acts as a sink for excess sample (FIG. 1, top). In a sandwich assay format, the LFA indicator (which can be colorimetric, fluorescent, radioactive, etc.) decorated with binding molecules (often antibodies, aptamers, single-stranded DNA, etc.) are first added to the sample. If the target analyte is present, it will bind to the indicator decorated with the antibodies. As these complexes are applied to the LFA test strip, e.g., through the sample pad, they flow through the strip towards the absorbent pad. If the target analyte is present, the analyte will bind to the binding molecules immobilized on the test line and become sandwiched between the indicator and the membrane. If the indicator is colorimetric, the colorimetric indicator will exhibit a strong color, and a visual band forms as the analyte-indicator complex accumulates at the test line, indicating a positive result. Alternatively, if no analyte is present, the indicator does not attach to the test line, and the absence of the test line indicates a negative result. Regardless of the presence of the analyte, the binding molecule decorated on the indicator can bind and accumulate on a control line (when present). A band at the control line signifies that the sample has flowed through the strip, indicating a valid test. A positive result is therefore indicated by two bands, one at the test line and one at the control line, while a negative result is indicated by a single band at the control line.

As described herein the detection limit of our previous integrated LFA and ATPS device is improved through the addition of a signal enhancement strategy that requires no additional user steps. The typical protocol for LFA signal enhancement first requires a sample solution to be applied to the LFA strip along with a colorimetric probe for 10-20 minutes. Next, a development reagent is applied to the LFA test strip to enhance the signal produced by the probe. In certain embodiments this enhancement can provide a 10-50 fold improvement in detection limit of the LFA only case.

In certain embodiments methods and devices are provided herein for the combination of manual ATPS extraction with the multistep signal enhancement. When an analyte is added and concentrated into one of the bulk phases of the ATPS, that phase can be manually (or robotically) extracted and applied to the LFA for detection. After, for example, 10-20 minutes, the user (or robot) can apply the development reagent to enhance the LFA signal. Due to compounding improvements in detection limit from ATPS concentration and signal enhancement, this multistep approach can improve the detection limit of LFA by 100-1000 fold. It is important that the colorimetric probe and the development reagent solutions stay separated from one another, as mixing can cause premature development resulting in a high background signal. While the above approach successfully keeps reagents separated, the need for multiple, timed steps increases test variability and decreases user friendliness.

Figure 2:
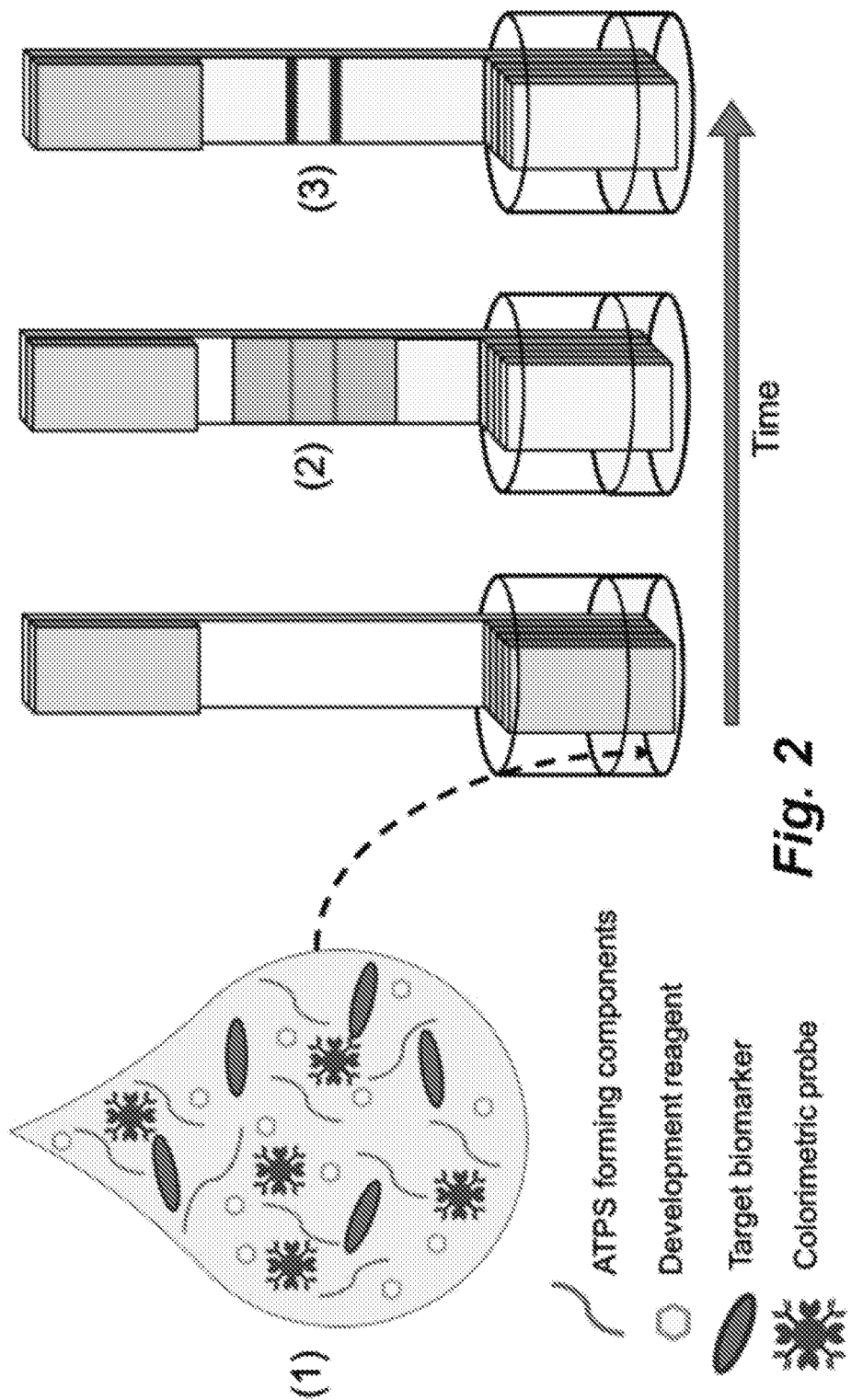
FIG. 2 schematically illustrates one embodiment of aqueous two phase system (ATPS) separation on paper used in combination with a lateral-flow assay (LFA) to concentrate a target analyte (e.g., a biomarker) and deliver development reagents to enhance the signal. As shown, an LFA strip is dipped into an ATPS solution (1) containing the target analyte (e.g., a biomarker), a probe (e.g., a colorimetric probe), and one or more development reagents. The ATPS will phase separate into leading and lagging phases. First, the leading phase (2) delivers the concentrated target analyte(s) (e.g., biomarkers) and colorimetric probes to the detection region. This is followed by the flow of the lagging phase (3) flowing across the detection zone, which delivers the development reagent to enhance LFA signal. Pink corresponds to the colorimetric probe, while yellow represents the development reagent.

In order to eliminate the need for multiple user steps while still keeping the colorimetric probe and development reagents separated, certain embodiments exploit the opposite partitioning behaviors of the probe and development reagents in various ATPSs, as well as, in certain embodiments, the phenomenon of ATPS separation on paper. In this approach, probes (e.g., colorimetric probes) can be engineered to partition extremely into the more hydrophilic and less crowded phase of the ATPS by increasing their size and/or hydrophilicity. This corresponds to the salt-rich phase in a polymer-salt ATPS or the micelle-poor phase in a micellar ATPS. Conversely, the small size and relative hydrophobicity of the developing reagent(s) results in partitioning to the more hydrophobic and crowded phase of the ATPS. This corresponds to the polymer-rich phase of a polymer-salt ATPS or the micelle-rich phase of the micellar ATPS. Application of the ATPS to a paper substrate will result in accelerated phase separation and the formation of a leading more hydrophilic phase and a lagging more hydrophobic phase. For a polymer-salt ATPS, this corresponds to a leading salt-rich phase and a lagging polymer-rich phase, while for a micellar ATPS, there is a leading micelle-poor phase and a lagging micelle-rich phase. The leading phase will deliver the concentrated biomarker and colorimetric probe to the detection zone of the LFA. This will be followed by the lagging phase which will deliver the development reagent to initiate signal enhancement (FIG. 2).

Figure 3:
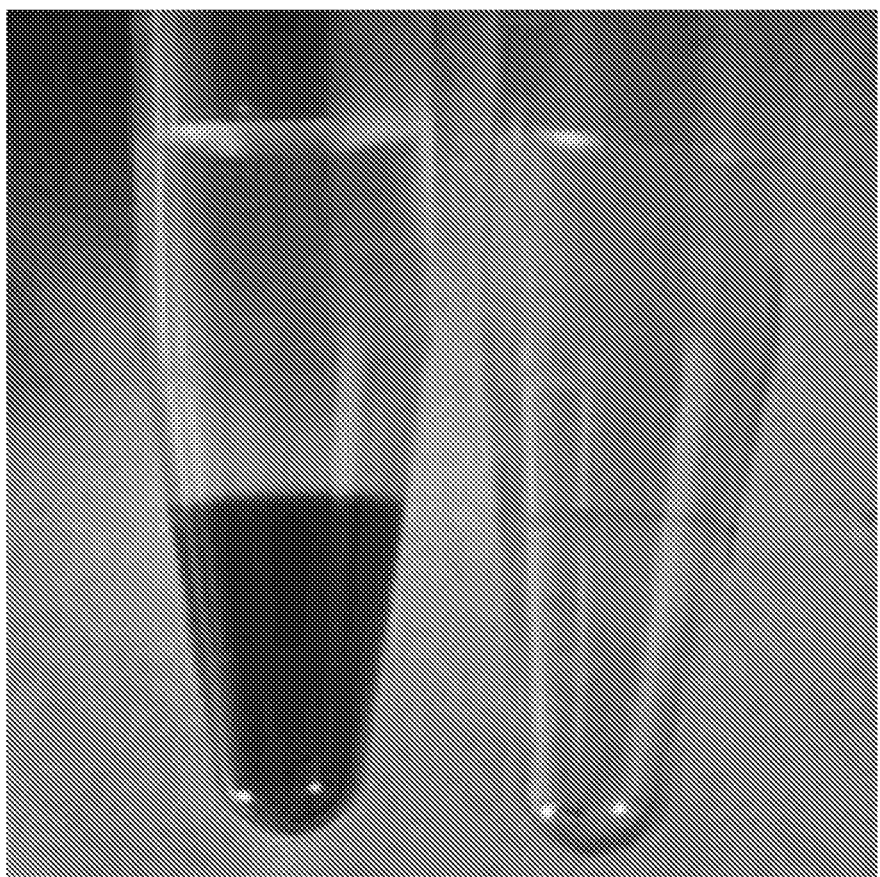
FIG. 3 shows ALP-GNPs partitioning extremely into the bottom, salt-rich phase of a PEG-salt ATPS (left) and NBT/BCIP partitioning extremely into the top, PEG-rich phase of a PEG-salt ATPS (right).
Figure 4:
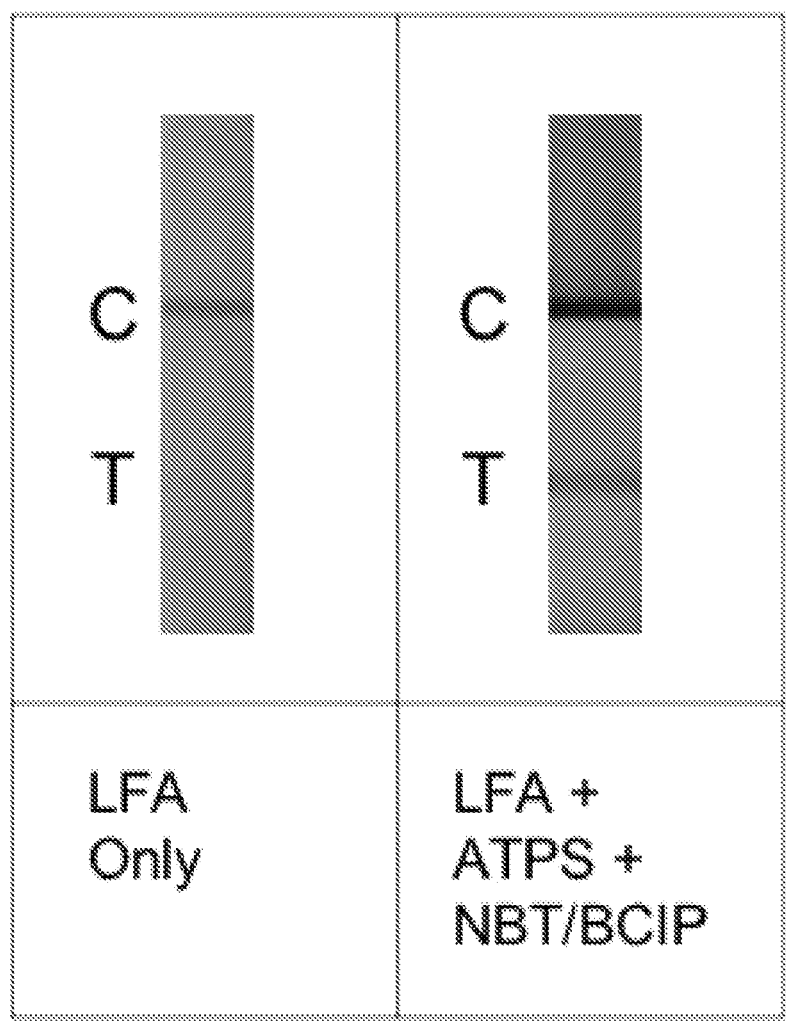
FIG. 4 illustrates detection of the model protein transferrin at low concentration with LFA only (left) compared with the new LFA+ATPS+NBT/BCIP design showing successful signal enhancement without any additional user steps.

We have demonstrated the feasibility of this approach using an enzymatic system based on the development of nitro-blue tetrazolium/5-bromo-4-chloro-3-inodyl phosphate (NBT/BCIP) by the enzyme alkaline phosphatase (ALP) for the detection of a model protein transferrin (Tf). ALP and anti-Tf antibodies were conjugated onto gold nanoparticles to form alkaline phosphatase-gold nanoprobes (ALP-GNPs). These ALP-GNPs can capture Tf in solution and drive it into a desired ATPS phase for concentration. They also serve as the colorimetric indicator for the LFA, but with the additional capability of being able to react with the NBT/BCIP substrate solution to produce a purple precipitate. Upon addition to a PEG-salt ATPS, ALP-GNPs partition into the bottom, salt-rich phase, while the NBT/BCIP substrate partitions into the top, PEG-rich phase (FIG. 3). When the ATPS is applied to our 3-D paper well with a downstream LFA test strip, the ALP-GNPs, along with the biomarker of interest, will be concentrated in the leading salt-rich phase and delivered to the detection zone. This will be followed by the PEG-rich phase flowing across the detection zone, delivering the NBT/BCIP substrate. The substrate will be converted into a purple precipitate by any ALP-GNPs that have bound to the detection zone, thereby enhancing the signal (FIG. 4). While we have demonstrated the feasibility of this approach using a PEG-salt ATPS with the ALP enzymatic reaction with NBT/BCIP, this technique can be applied to other ATPS systems (e.g., PPG-salt, PEG-dextran, Triton X-114, $C_{10}E_4$, etc.) and signal enhancement systems (horseradish peroxidase and peroxidase-like nanoparticles with TMB or DAB, gold and silver enhancement, etc.). It is believed this approach can achieve 100-1000 fold improvements in detection limit over traditional LFA with just a single user application step.

While the foregoing methods are described with reference to LFAs, it will be recognized that they can easily also be applied to flow through assays, e.g. assays such as that shown in FIG. 11.

While in certain embodiments, the ATPS, probes, and development reagent(s) are selected so that the probes are in a leading phase and the development reagent(s) are provided in a lagging phase, embodiments are also contemplated wherein the probe(s) localize at the interface between the two phases and development reagent(s) are provided in the lagging phase.

Combination of Nucleic Acid Amplification with Nucleic Acid Concentration and Pre-Concentration.

In certain embodiments methods and devices are provided that combine DNA amplification technology with DNA extraction and pre-concentration steps, all into one unified platform. In certain embodiments this platform consists of an aqueous two-phase system (ATPS), which, at given component concentrations and temperatures, will allow the ATPS mixture to separate into two distinct phases. Both phases are aqueous, and provide a stable environment for biomolecules.

Figure 5:
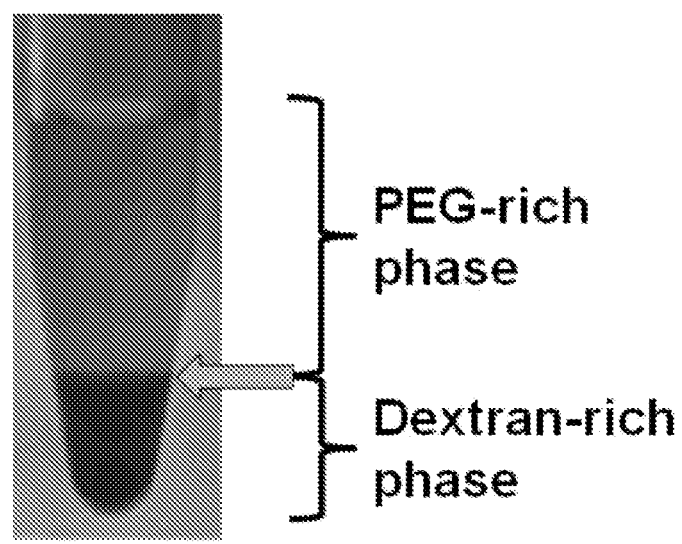
FIG. 5 shows a visual demonstration of blood partitioning in a PEG-Dextran ATPS.
Figure 6:
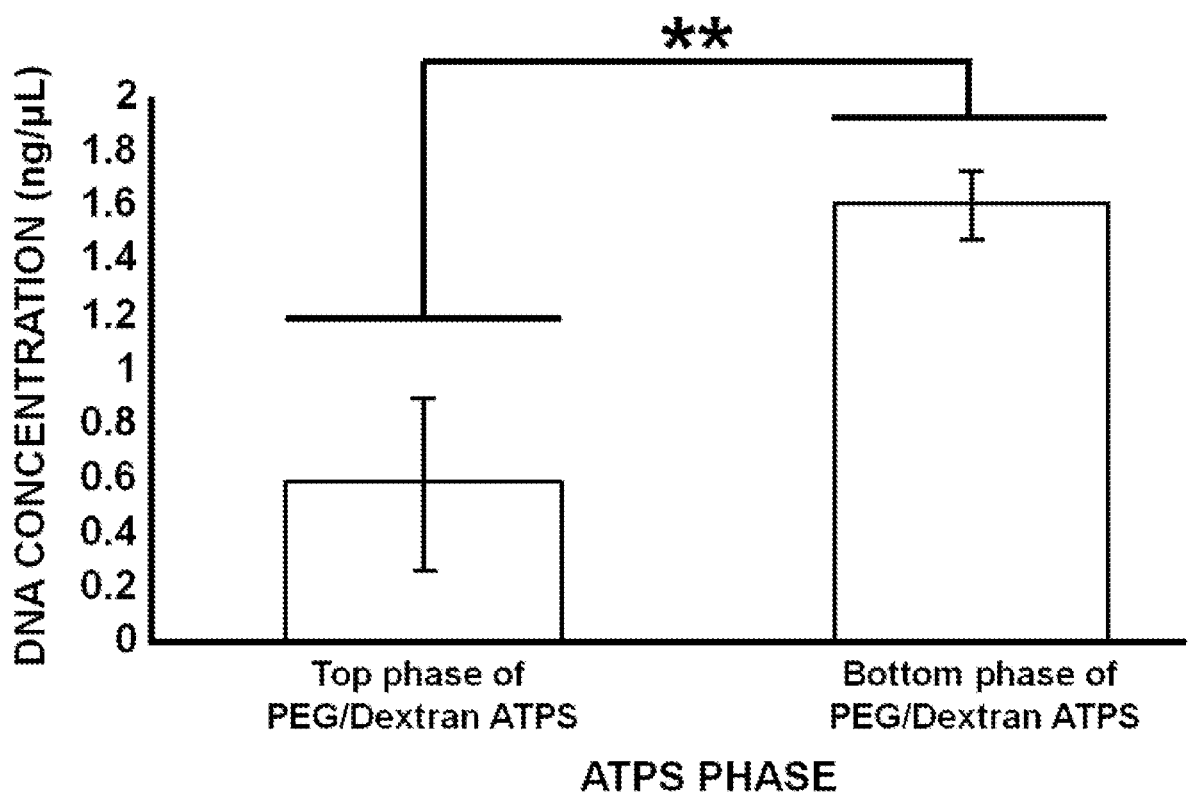
FIG. 6 shows the concentration of DNA eluted from dried blood spots in the PEG/Dextran ATPS. DNA concentrations measured using the Quant-iT™ fluorescence assay showed a significantly greater concentration of DNA in the bottom phase compared to the top phase of the PEG/Dextran ATPS ($p<0.01$, $n=3$). These results show DNA elution from dried blood spots (DBS) made on fiberglass paper treated with trehalose and bovine serum albumin (BSA).

ATPSs have diverse properties and suit a range of biological purposes, such as sample purification and cell lysis, as well as biomolecule separation, sorting, and concentration. For example, a micellar ATPS made with Triton surfactant can partition biomolecules, like DNA, extremely to one phase. Moreover, Triton surfactant is also known to have inherent cell lysis capability. Alternatively, an ATPS made from polyethylene glycol (PEG) and dextran can be used to resolubilize dried blood spots and partition blood cells into one phase (see, e.g., FIG. 5). The DNA from resolubilized blood cells can be subsequently concentrated into the bottom, dextran-rich phase (FIG. 6). Often, preparing and extracting DNA from a complex biological sample in order to be amplified requires these cell lysis, DNA purification, and concentration steps. Because these outcomes are achievable with an ATPS, this makes the ATPS an appropriate biological sample manipulation platform to integrate with DNA amplification and/or other protocols.

Figure 7:
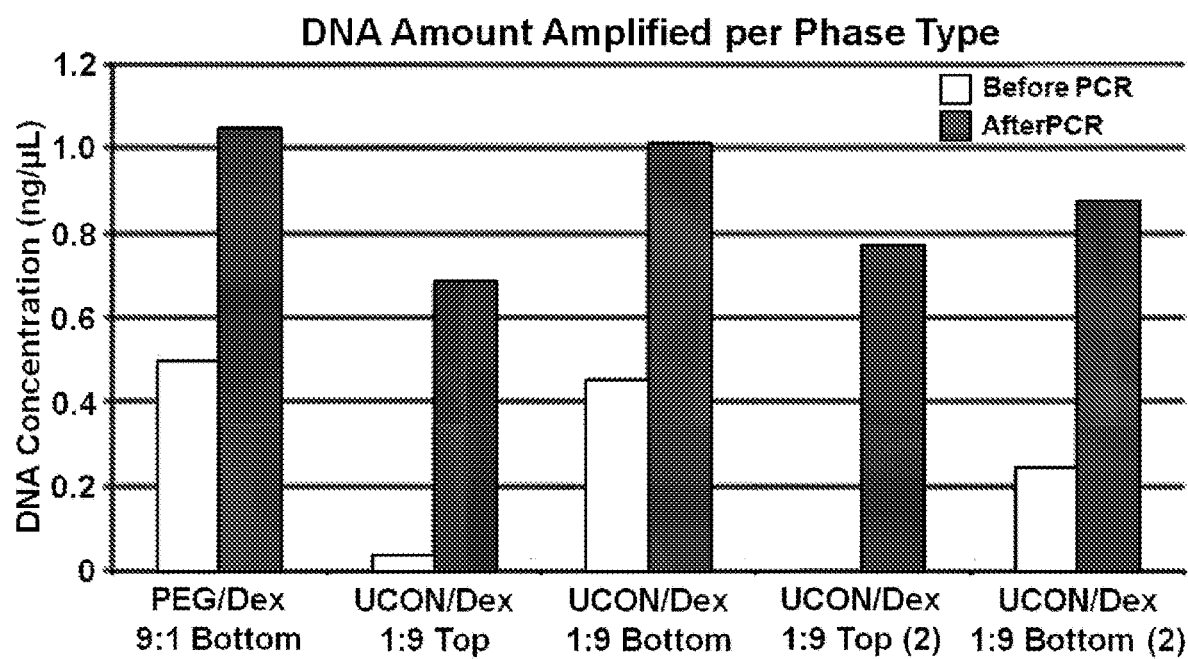
FIG. 7 illustrates a comparison of DNA concentration in the bottom, dextran-rich phase of PEG/Dextran ATPS, and both phases of the UCON/Dextran ATPS, before and after amplification. Amplification was achieved in all the phase compositions tested. The 9:1 and 1:9 ratios denote the volume ratios of the top to bottom phases.
Figure 8:
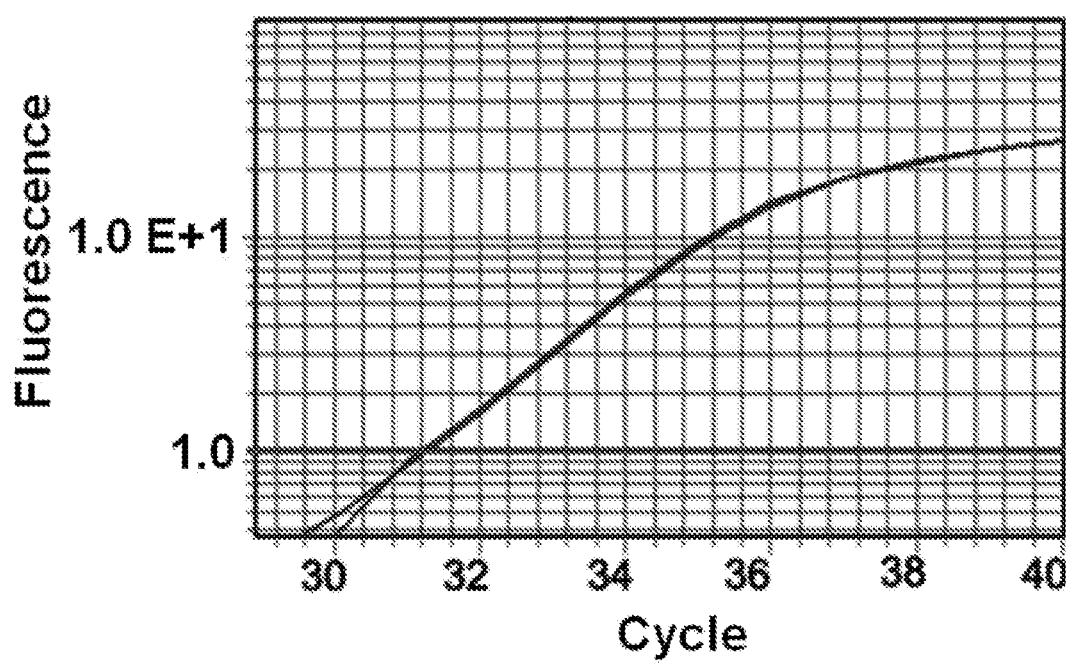
FIG. 8 shows average qPCR amplification cycle number of DNA with and without the presence of ATPS polymers. Amplification plots (shown in purple) for DNA in water and DNA in the bottom, dextran-rich phase of a PEG/dextran ATPS were generated from fluorescence intensity of the reporter dye. The green line on the plot indicates the threshold fluorescence intensity of the reporter dye. The cycle number at the intersection of the purple amplification curves and the fluorescence threshold, also known as the threshold cycle, indicates the concentration of target DNA in the qPCR reaction. The average threshold cycle numbers for amplification of DNA in water and amplification of DNA in the dextran-rich phase of the PEG/dextran ATPS are 32 and 31, respectively. Cycle numbers were compared using a student t-test ($p<0.01$, $n=3$) and showed no statistical significance between the two methods.

In one illustrative approach to integrate ATPS DNA extraction/pre-concentration and nucleic acid (e.g., DNA) amplification one of the ATPS phases or the interface containing the concentrated nucleic can be extracted and directly added to a nucleic acid amplification reaction containing buffer reagents, salt solutions, nucleotide bases, enzymes, and primers specific for amplifying a target nucleic acid (e.g., DNA template). In one example, a blood-compatible polymerase was used to successfully amplify DNA directly from a dextran-rich phase and a UCON-rich phase. Upon amplification, a 2- to 7-fold increase in DNA concentration was achievable, indicating that the polymerase was compatible with the ATPS systems tested (FIG. 7). Conventional quantitative polymerase chain reaction (qPCR) was also performed directly on DNA in a dextran-rich phase, and was able to proceed as successfully as amplification from DNA in pure water (FIG. 8).

Another illustrative, but non-limiting approach involves combining all the components required for both ATPS and nucleic acid (e.g., DNA) amplification into one mixture. Notably, this method can typically utilize isothermal nucleic acid (e.g., DNA amplification). While the commonly used polymerase chain reaction (PCR) amplification method cycles through different temperatures for each step of the DNA amplification process, isothermal amplification allows the entire DNA amplification process to be performed at one set temperature. An example of this is thermophilic helicase dependent amplification (tHDA), which uses helicase to separate double-stranded DNA rather than heat cycling, allowing amplification to be performed isothermally at, for example, 65° C. Since there are micellar ATPSs that also phase separate at this temperature, they can be combined with the tHDA reaction components to facilitate simultaneous DNA concentration and amplification.

Figure 9:
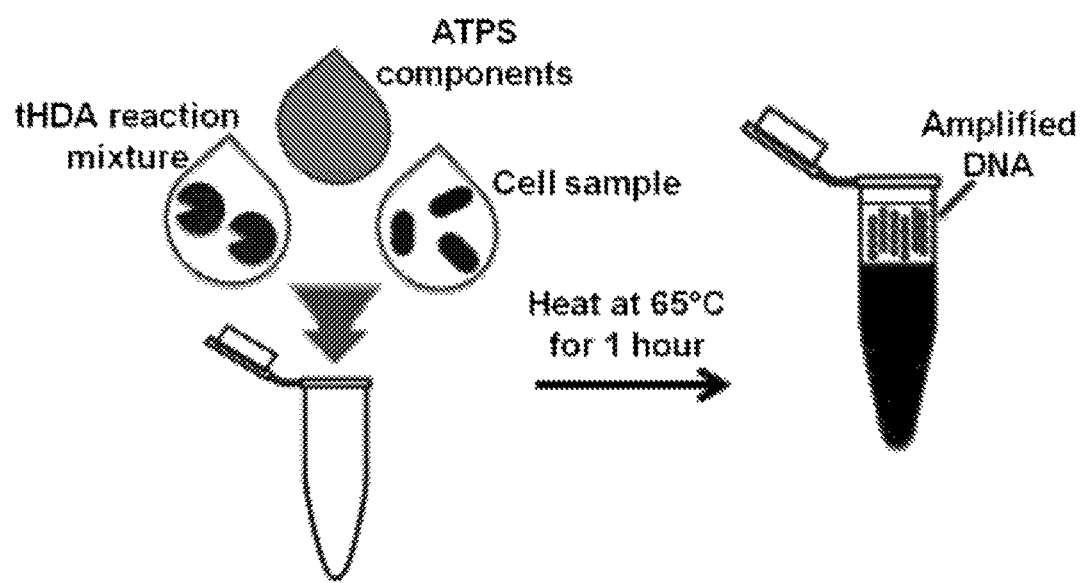
FIG. 9 illustrates a schematic of one embodiment of DNA amplification using a one-pot ATPS and tHDA reaction.
Figure 10:
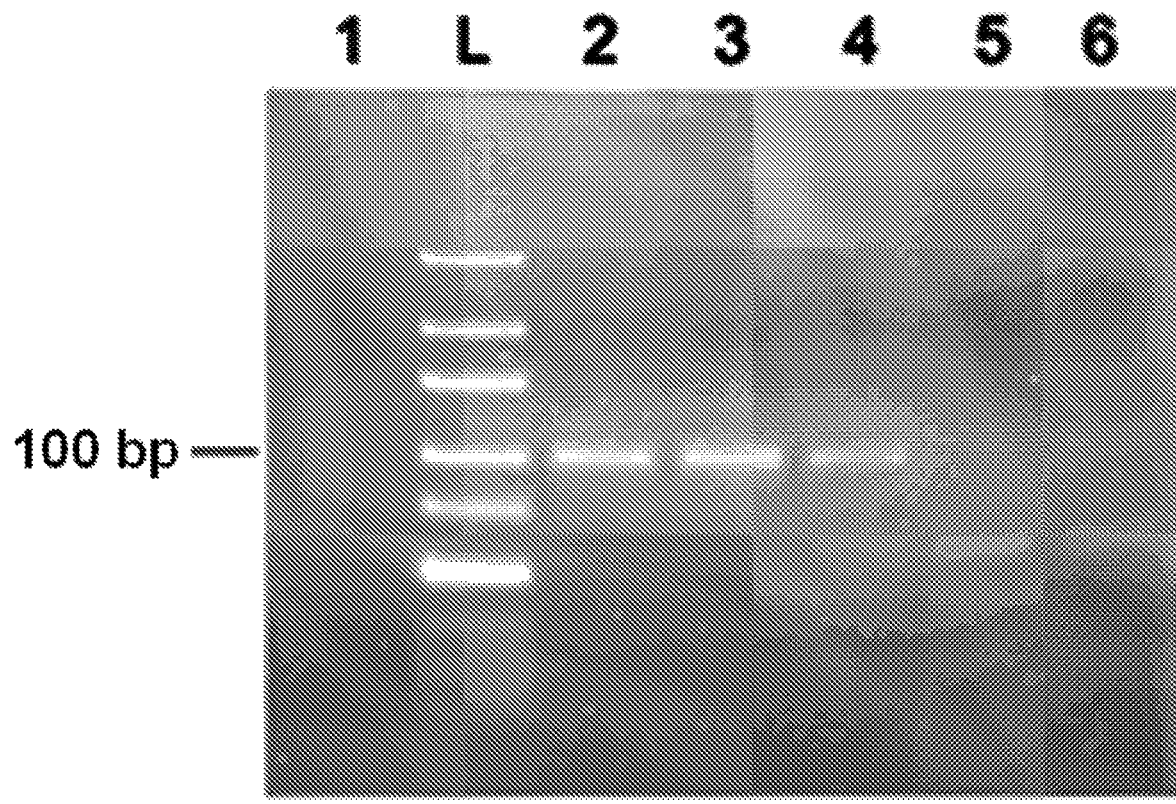
FIG. 10 shows a comparison of a one-pot ATPS and tHDA reaction with the tHDA-only reaction. Lane 1 shows no amplification from $7.7\times10^4$ cells with tHDA-only. Lanes 2-4 show successful amplification of a 100 bp target product using the one-pot reaction with samples containing $7.7\times10^4$, $1.6\times10^4$ cells, and $1.7\times10^3$ cells, respectively. In lanes 5 and 6, the one-pot reaction was performed with 102 cells, where lane 6 accurately shows the presence of the 100 bp target band. The secondary band that appears in lanes 5 and 6 is a non-specific artifact byproduct of performing amplification when the number of cells drops below a threshold value.

To do this, a whole-cell sample can be added into the combined solution, upon which the entire solution can then be mixed to form a micellar ATPS. The mixture is then heated at, e.g., 65° C. for 1 hour, which allows for both phase separation and DNA amplification to occur (FIG. 9). The nucleic acid (e.g., DNA) is partitioned into one of the two phases, from which the amplified DNA can then be extracted. The ability to both concentrate and amplify a nucleic acid concurrently in this one-pot platform allows amplification to be achieved from samples with fewer cells than possible for the current tHDA technology alone. The current tHDA technology successfully amplifies DNA from a sample with 10,000+ cells. Conversely, our preliminary results have shown that DNA can be successfully amplified from a sample with as few as 100 cells using the combined Triton X-100 ATPS and tHDA one-pot system (FIG. 10). Meanwhile, the tHDA system itself can only achieve this same low detection limit when a cell sample is separately lysed and the DNA is purified and concentrated via commercial kits and other laboratory equipment. Thus, our one-pot platform's improved sensitivity and simplicity makes it a competitive candidate for point-of-care nucleic acid amplification test (NAAT)-based disease detection. Our invention is also very versatile as there are many possible ATPSs and isothermal amplification reagents that can be used.

Concentration of the Target Biomolecules

In various embodiments of the assays described herein, the analytes (e.g., target biomolecules) can be concentrated using an aqueous two phase system (ATPS). In various embodiments the ATPS can be performed in either bulk liquid form (e.g., in a vessel), or as the sample solution flows in a lateral-flow assay or a flow through assay, e.g., in paper membranes.

Concentration in Liquid ATPS

A collected sample, (e.g., a tissue sample, a biological fluid such as urine, saliva, and blood, sputum, vaginal fluid, seminal fluid, cerebrospinal fluid, lymph, endocervical swab, plaque from teeth, a food sample, and environmental sample, and the like), can, optionally, be combined with a suspending solution (e.g., a buffer) or combined directly with an ATPS solution or directly applied to a paper or a suspending solution containing the sample applied to a paper to rehydrate ATPS components that were previously dried onto paper. In some cases, mixing by the user may be required to achieve a well-mixed, homogeneous solution. In various illustrative, but non-limiting embodiments polymer/salt, polymer/polymer, micellar/polymer, or micellar ATPS may be used.

Concentration as Fluid Flows on Paper

In various embodiments the concentration step can also be accelerated with paper. For example, the collected specimen can be mixed with ATPS components and introduced to a paper device that can facilitate, enhance, and accelerate phase separation. The target biomolecules can be concentrated in the leading front of the flow on the paper membrane and can seamlessly be introduced to the subsequent detection component.

Alternatively, the ATPS components can be pre-dehydrated onto the paper membranes. In this case, the collected specimen can be directly applied to the paper membrane without pre-mixing with the ATPS components.

Aqueous Two Phase System (ATPS)

In certain embodiments the devices described herein are configured to work in conjunction with an aqueous two-phase system (ATPS), e.g., in a syringe or other vessel, or they are configured to support an aqueous two-phase system (ATPS). In some embodiments, the ATPS comprises a phase solution. The term "phase solution" generally refers to a first phase solution or a second phase solution of the ATPS. In some embodiments, the phase solution is in a mixed solution (e.g. with the first/second phase solution). In some embodiments, the phase solution is the first/second phase solution after it partitions from the mixed solution of the ATPS. In some embodiments, the phase solution is the first/second phase solution after it partitions from the mixed solution in the LFA or flow-through assay. In certain embodiments the phase solution can refer to the second phase solution while it is in a mixed state (e.g. with the first phase solution). In some embodiments, the phase solution is a leading fluid in the LFA or flow-through assay. In some embodiments, the phase solution is a lagging fluid in the LFA or flow-through assay.

In some embodiments, the ATPS comprises two aqueous solutions, a first phase solution and a second phase solution that are initially mixed (e.g., a mixed phase solution). In some embodiments, the mixed phase solution is a homogeneous solution, while in certain other embodiments the first phase solution and the second phase solution are immiscible. In some embodiments, the first phase solution and the second phase solution are immiscible, but domains of the first phase solution are mixed with domains of the second phase solution. In some embodiments, the immiscibility is driven by changes in temperature, and/or changes in the concentrations of the different components, such as salt. In some embodiments, the first/second phase solutions comprise components, such as, micelles, salts, and/or polymers. In some embodiments, the target analyte (e.g., biomolecule, bacterium (or fragment thereof), fungus (or fragment thereof), or virus, and the like) in contact with the ATPS, distributes, partitions, and/or concentrates preferentially into the first phase solution over the second phase solution, or vice versa, based on its physical and chemical properties, such as size, shape, hydrophobicity, and charge. In some embodiments, the target analyte (e.g. a bacterium, fungus, virus, etc.) partitions predominantly (or extremely) into the first or second phase solution of the ATPS, and therefore concentrates in the ATPS. In some embodiments, the target analyte is concentrated by adjusting the ratio of volumes between the first phase solution and the second phase solution. In some embodiments, the target analyte is concentrated by reducing the volume of the phase in which the analyte partitions. By way of illustration, in some embodiments, the target analyte is concentrated by 10-fold in the first phase solution, e.g., by using a 1:9 volume ratio of first phase solution to second phase solution, since the volume of the phase into which the analyte extremely partitions into is $\frac{1}{10}$ the total volume.

In some embodiments, other concentrations are obtained by using other ratios. Thus, in some embodiments the ratio of the first phase solution to the second phase solution comprises a ratio of about 1:1, about 1:2, about 1:3, about 1:4, about 1:5, about 1:6, about 1:7, about 1:8, about 1:9, or about 1:10. In some embodiments the ratio of the first phase solution to the second phase solution comprises a ratio of about 1:20, about 1:30, about 1:40, about 1:50, about 1:60, about 1:70, about 1:80, about 1:90, or about 1:100. In some embodiments the ratio of the first phase solution to the second phase solution comprises a ratio of about 1:200, about 1:300, about 1:400, about 1:500, about 1:600, about 1:700, about 1:800, about 1:900, or about 1:1000.

In some embodiments the ratio of the second phase solution to the first phase solution comprises a ratio of about 1:1, about 1:2, about 1:3, about 1:4, about 1:5, about 1:6, about 1:7, about 1:8, about 1:9, or about 1:10. In some embodiments the ratio of the second phase solution to the first phase solution comprises a ratio of about 1:20, about 1:30, about 1:40, about 1:50, about 1:60, about 1:70, about 1:80, about 1:90, or about 1:100. In some embodiments the ratio of the second phase solution to the first phase solution comprises a ratio of about 1:200, about 1:300, about 1:400, about 1:500, about 1:600, about 1:700, about 1:800, about 1:900, or about 1:1000.

In some embodiments, the analyte partitions substantially evenly between the first phase solution and second phase solution, preventing concentration of the analyte. In such systems, concentration of the target analyte are achieved by introducing an additional component, such as a probe that captures the target analyte, and wherein the probe partitions predominantly into one phase, thereby enhancing the partitioning behavior of the target analyte to enable concentration. In some embodiments, the first/second phase solution containing the concentrated analyte is collected and applied to the LFA or to the flow-through assay device.

In some embodiments, the first/second phase solution comprises a micellar solution. In some embodiments, the micellar solution comprises a nonionic surfactant. In some embodiments, the micellar solution comprises a detergent. In some embodiments, the micellar solution comprises the nonionic surfactant TRITON-X®. In some embodiments, the micellar solution comprises a polymeric non-ionic surfactant similar to TRITON-X®, such as IGEPAL CA-630® and NONIDET P-40®, and the like, by way of non-limiting example. In some embodiments, the micellar solution consists essentially of TRITON-X®.

In some embodiments, the micellar solution has a viscosity (at room temperature (~25° C.) of about 0.01 centipoise to about 5000 centipoise, about 0.01 centipoise to about 4500 centipoise, about 0.01 centipoise to about 4000 centipoise, about 0.01 centipoise to about 3500 centipoise, about 0.01 centipoise to about 3000 centipoise, about 0.01 centipoise to about 2500 centipoise, about 0.01 centipoise to about 2000 centipoise, about 0.01 centipoise to about 1500 centipoise, about 0.01 centipoise to about 1000 centipoise, or about 0.01 centipoise to about 500 centipoise. In some embodiments, the micellar solution has a viscosity at room temperature of about 0.01 centipoise to about 450 centipoise, about 0.01 centipoise to about 400 centipoise, about 0.01 centipoise to about 350 centipoise, about 0.01 centipoise to about 300 centipoise, about 0.01 centipoise to about 250 centipoise, about 0.01 centipoise to about 200 centipoise, about 0.01 centipoise to about 150 centipoise, or about 0.01 centipoise to about 100 centipoise.

In some embodiments, the rehydrated first/second phase solution comprises a polymer (e.g., polymer solution). In certain embodiments the polymer comprises one or more polymers selected from the group consisting of polyethylene glycol (PEG), ethylene/propylene copolymer (e.g., a UCON™ polymer), propylene glycol (PPG), methoxypolyethylene glycol, polyvinyl pyrrolidone, and the like. In certain embodiments, the polymer is a polyethylene glycol (PEG). In various embodiments, the PEG may have a molecular weight between 1000 and 100,000. In certain embodiments, the PEG comprises PEG-4600, PEG-8000, or PEG-20,000. In certain embodiments, the polymer is polypropylene glycol (PPG). In various embodiments, the PPG may have a molecular weight between 100 and 10,000. In certain embodiments, the PPG comprises PPG 425. In certain embodiments, the polymer is dextran. In various embodiments, the dextran may have a molecular weight between 1000 and 1,000,000. In certain embodiments, the dextran comprises dextran 6000, dextran 9000, dextran-35,000, or dextran-200,000. In certain embodiments the polymer comprises an ethylene/propylene copolymer (e.g., a UCON™ polymer). Illustrative, but non-limiting ethylene/propylene copolymers include, but are not limited to UCON™ 50-HB-5100, UCON™ 50-HB-3520, UCON™ 50-HB-2000, UCON™ 50-HB-660, UCON™ 50-HB-400, UCON™ 50-HB-260, UCON™ 50-HB-170, UCON™ 50-HB-100, UCON™ 60-H-5300, UCON™ 60-H2300, UCON™ 60-H-1600, UCON™ 60-H-1100, UCON™ 60-H-760, UCON™ 60-H-340, UCON™ 75-H-9500, UCON™ 75-H-1400, UCON™ 75-H-450, and the like.

In some embodiments, the rehydrated polymer solution comprises a polymer solution that is about 0.01% w/w polymer, or about 0.05% w/w polymer, or about 0.1% w/w polymer, or about 0.15% w/w polymer, or about 0.2% w/w polymer, or about 0.25% w/w polymer, or about 0.3% w/w polymer, or about 0.35% w/w polymer, or about 0.4% w/w polymer, or about 0.45% w/w polymer, or about 0.5% w/w polymer, or about 0.55% w/w polymer, or about 0.6% w/w polymer, or about 0.65% w/w polymer, or about 0.7% w/w polymer, or about 0.75% w/w polymer, or about 0.8% w/w polymer, or about 0.85% w/w polymer, or about 0.9% w/w polymer, or about 0.95% w/w polymer, or about 1% w/w polymer. In some embodiments, the polymer solution comprises a polymer solution that is about 1% w/w polymer, or about 2% w/w polymer, or about 3% w/w polymer, or about 4% w/w polymer, or about 5% w/w polymer, or about 6% w/w polymer, or about 7% w/w polymer, or about 8% w/w polymer, or about 9% w/w polymer, or about 10% w/w polymer, or about 11% w/w polymer, or about 12% w/w polymer, or about 13% w/w polymer, or about 14% w/w polymer, or about 15% w/w polymer, or about 16% w/w polymer, or about 17% w/w polymer, or about 18% w/w polymer, or about 19% w/w polymer, or about 20% w/w polymer, or about 21% w/w polymer, or about 22% w/w polymer, or about 23% w/w polymer, or about 24% w/w polymer, or about 25% w/w polymer, or about 26% w/w polymer, or about 27% w/w polymer, or about 28% w/w polymer, or about 29% w/w polymer, or about 30% w/w polymer, or about 31% w/w polymer, or about 32% w/w polymer, or about 33% w/w polymer, or about 34% w/w polymer, or about 35% w/w polymer, or about 36% w/w polymer, or about 37% w/w polymer, or about 38% w/w polymer, or about 39% w/w polymer, or about 40% w/w polymer, or about 41% w/w polymer, or about 42% w/w polymer, or about 43% w/w polymer, or about 44% w/w polymer, or about 45% w/w polymer, or about 46% w/w polymer, or about 47% w/w polymer, or about 48% w/w polymer, or about 49% w/w polymer, or and about 50% w/w polymer. In some embodiments, the polymer solution comprises a polymer solution that is about 10% w/w polymer, or about 20% w/w polymer, or about 30% w/w polymer, or about 40% w/w polymer, or about 50% w/w polymer, or about 60% w/w polymer, or about 70% w/w polymer, or about 80% w/w polymer, or about 90% w/w polymer. In some embodiments, the polymer solution comprises a polymer solution that is about 10% w/w polymer to about 80% w/w polymer. In some embodiments, the rehydrated polymer solution comprises a polymer solution that is about 1% w/w to about 30% w/w, or from about 5% w/w up to about 25% w/w, or from about 10% w/w up to about 25% w/w, or from about 10% w/w up to about 20% w/w polymer.

In some embodiments, the rehydrated first and/or second phase solution comprises a salt and thereby forms a salt solution. In some embodiments, the target analyte (e.g., bacterium, fungus, virus, etc.) and/or a probe-analyte complex partitions into the salt solution. In certain embodiments the salt solution comprises a kosmotropic salt. In some embodiments the salt solution comprises a chaotropic salt. In some embodiments, the salt comprises one or more of a magnesium salt, a lithium salt, a sodium salt, a potassium salt, a cesium salt, a zinc salt, and an aluminum salt. In some embodiments, the salt comprises a bromide salt, an iodide salt, a fluoride salt, a carbonate salt, a sulfate salt, a citrate salt, a carboxylate salt, a borate salt, or a phosphate salt. In some embodiments, the salt is potassium phosphate. In some embodiments, the salt is ammonium sulfate.

In some embodiments, the rehydrated salt solution comprises a salt solution comprising about 0.01% w/w salt, or about 0.05% w/w salt, about 0.1% w/w salt, or about 0.15% w/w salt, or about 0.2% w/w salt, or about 0.25% w/w salt, or about 0.3% w/w salt, or about 0.35% w/w salt, or about 0.4% w/w salt, or about 0.45% w/w salt, or about 0.5% w/w salt, or about 0.55% w/w salt, or about 0.6% w/w salt, or about 0.65% w/w salt, or about 0.7% w/w salt, or about 0.75% w/w salt, or about 0.8% w/w salt, or about 0.85% w/w salt, or about 0.9% w/w salt, or about 0.95% w/w salt, or about or about 1% w/w salt. In some embodiments, the rehydrated salt solution comprises a salt solution that is about 1% w/w salt, or about 2% w/w salt, or about 3% w/w salt, or about 4% w/w salt, or about 5% w/w salt, or about 6% w/w salt, or about 7% w/w salt, or about 8% w/w salt, or about 9% w/w salt, or about 10% w/w salt, or about 11% w/w salt, or about 12% w/w salt, or about 13% w/w salt, or about 14% w/w salt, or about 15% w/w salt, or about 16% w/w salt, or about 17% w/w salt, or about 18% w/w salt, or about 19% w/w salt, or about 20% w/w salt, or about 21% w/w salt, or about 22% w/w salt, or about 23% w/w salt, or about 24% w/w salt, or about 25% w/w salt, or about 26% w/w salt, or about 27% w/w salt, or about 28% w/w salt, or about 29% w/w salt, or about 30% w/w salt, or about 31% w/w salt, or about 32% w/w salt, or about 33% w/w salt, or about 34% w/w salt, or about 35% w/w salt, or about 36% w/w salt, or about 37% w/w salt, or about 38% w/w salt, or about 39% w/w salt, or about 40% w/w salt, or about 41% w/w salt, or about 42% w/w salt, or about 43% w/w salt, or about 44% w/w salt, or about 45% w/w salt, or about 46% w/w salt, or about 47% w/w salt, or about 48% w/w salt, or about 49% w/w salt, or and about 50% w/w. In some embodiments, the rehydrated salt solution comprises a salt solution that ranges from about 0.1% w/w to about 40% w/w, or from about 1% w/w up to about 30% w/w, or from about 5% w/w up to about 25% w/w, or from about 10% w/w up to about 20% w/w. In some embodiments, the rehydrated salt solution comprises a salt solution that is about 0.1% w/w to about 10%. In some embodiments, the salt solution is about 1% w/w to about 10%.

In some embodiments, the first/second phase solution comprises a solvent that is immiscible with water. In some embodiments, the solvent comprises a non-polar organic solvent. In some embodiments, the solvent comprises an oil. In some embodiments, the solvent comprises pentane, cyclopentane, benzene, 1,4-dioxane, diethyl ether, dichloromethane, chloroform, toluene, or hexane.

In some embodiments, the first phase solution comprises a micellar solution and the second phase solution comprises a polymer. In some embodiments, the second phase solution comprises a micellar solution and the first phase solution comprises a polymer. In some embodiments, the first phase solution comprises a micellar solution and the second phase solution comprises a salt. In some embodiments, the second phase solution comprises a micellar solution and the first phase solution comprises a salt. In some embodiments, the micellar solution is a TRITON-X® solution. In some embodiments, the first phase solution comprises a first polymer and the second phase solution comprises a second polymer. In some embodiments, the first/second polymer comprises polyethylene glycol and/or dextran. In some embodiments, the first phase solution comprises a polymer and the second phase solution comprises a salt. In some embodiments, the second phase solution comprises a polymer and the first phase solution comprises a salt. In some embodiments, the first phase solution comprises polyethylene glycol and the second phase solution comprises potassium phosphate. In some embodiments, the second phase solution comprises polyethylene glycol and the first phase solution comprises potassium phosphate. In some embodiments, the first phase solution comprises a salt and the second phase solution comprises a salt. In some embodiments, the first phase solution comprises a kosmotropic salt and the second phase solution comprises a chaotropic salt. In some embodiments, the second phase solution comprises a kosmotropic salt and the first phase solution comprises a chaotropic salt.

In some embodiments, the first phase solution comprises a Component 1 of Table 1 and the second phase solution comprises a Component 2 of Table 1. In some embodiments, the second phase solution comprises a Component 1 of Table 1 and the second phase solution comprises a Component 2 of Table 1.

In some embodiments, the components of Table 1 are suspended or dissolved in a buffer. In some embodiments, the components of Table 1 are suspended/dissolved in a buffer compatible with a biological system from which the sample was derived. In some embodiments, the components of Table 1 are suspended/dissolved in a saline solution. In some embodiments, the components of Table 1 are suspended/dissolved in PBS. In some embodiments, the components of Table 1 are suspended/dissolved in water. In some embodiments, the components of Table 1 are suspended/dissolved in the biological fluid.

TABLE 1

Illustrative aqueous two-phase extraction/concentration systems.

| Component 1 | Component 2 |
|---|---|
| Polymer/polymer Systems | |
| Polyethylene glycol | Any one or more of: Dextran Ficoll Polyvinyl pyrrolidone Polyvinyl alcohol Hydroxypropyl starch |
| Polypropylene glycol | Any one or more of: Dextran Hydroxypropyl dextran Polyvinyl pyrrolidone |
| Polyvinyl alcohol | Any one or more of: Dextran Hydroxypropyl dextran |
| Polyvinyl pyrrolidone | Any one or more of Dextran Maltodextrin |
| Methyl cellulose | Any one or more of: Dextran Hydroxypropyl dextran |
| Ethylhydroxyethyl cellulose | Dextran |
| Polymer/salt Systems | |
| Any one or more of: Polyethylene glycol (PEG) Ethylene/propylene copolymer (e.g., UCON ™) Propylene glycol (PPG) Methoxypolyethylene glycol Polyvinyl pyrrolidone | Any one or more of: Potassium phosphate Sodium sulfate Magnesium sulfate Ammonium sulfate Sodium citrate Magnesium chloride Magnesium citrate Magnesium phosphate Sodium chloride Potassium citrate Potassium carbonate |
| Polyethylene glycol | Any one or more of: Potassium phosphate Sodium sulfate Magnesium sulfate Ammonium sulfate Sodium citrate Magnesium chloride Magnesium citrate Magnesium phosphate Sodium chloride Potassium citrate Potassium carbonate |
| Polyethylene glycol (PEG) | Potassium phosphate |
| Propylene glycol (PPG) | Potassium phosphate |
| Methoxypolyethylene glycol | Potassium phosphate |
| Polyvinyl pyrrolidone | Potassium phosphate |
| Ethylene/propylene copolymer (e.g., UCON ™ 50-HB-5100, UCON ™ 50-HB-3520, UCON ™ 50-HB-2000, UCON ™ 50-HB-660, UCON ™ 50-HB-400, UCON ™ 50-HB-260, UCON ™ 50-HB-170, UCON ™ 50-HB-100, UCON ™ 60-H-5300, UCON ™ 60-H2300, UCON ™ 60-H-1600, UCON ™ 60-H-1100, UCON ™ 60-H-760, UCON ™ 60-H-340, UCON ™ 75-H-9500, UCON ™ 75-H-1400, UCON ™ 75-H-450, etc.) | Potassium phosphate |

It will be noted that UCON' polymers comprise ethylene/propylene copolymers produced by reacting an equal amount by weight of ethylene oxide and propylene oxide with butyl alcohol using an alkali catalyst at temperatures from about 100° C. to about 150° C. The resulting UCON' 50-HB is a random copolymer with the general structure:

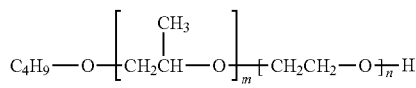

It will be recognized that the above-described ATPS systems and components are illustrative and non-limiting. Using the teachings provided herein, numerous other ATPS systems and components will be available to one of skill in the art.

In some embodiments, the devices described herein (e.g., an LFA or a flow-through assay device) can further comprise a collector configured to be placed in contact with the ATPS, wherein the target analyte partitions at an interface of the collector and the first phase solution and/or second phase solution. In some embodiments, the collector comprises a material that is a plastic, a mesoporous material, a silica, a polypropylene, a magnet, a magnetic particle, a paramagnetic particle, a material with a pore, a material with a groove, and/or any combination thereof. In some embodiments, the collector comprises polypropylene. In some embodiments, collector is optimized to increase target analyte collection. In some embodiments, the collector comprises a pore to maximize the surface area. In some embodiments, the width of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the width of the pore is about 100 µm, about 200 µm, about 300 µm, about 400 µm, about 500 µm, about 600 µm, about 700 µm, about 800 µm, about 900 µm, or about 1 mm. In some embodiments, the depth of the pore is about 1 µm, about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, or about 100 µm. In some embodiments, the depth of the pore is about 100 µm, about 200 µm, about 300 µm, about 400 µm, about 500 µm, about 600 µm, about 700 µm, about 800 µm, about 900 µm, or about 1 mm.

Detection of Target Analytes (e.g., Biomolecules)

Figure 11:
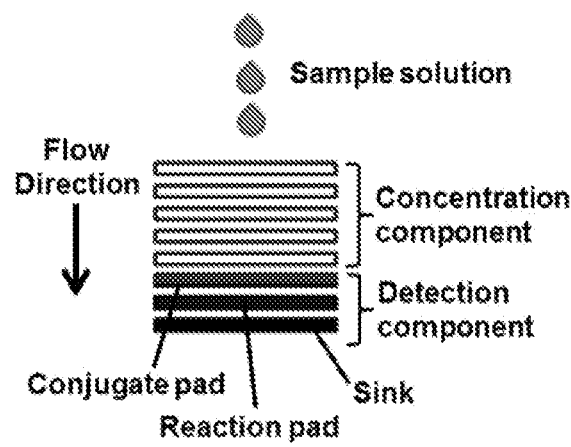
FIG. 11 shows a schematic one embodiment of an all-in-one spot test for the detection of target analytes (e.g., biomolecules). ATPS components and colorimetric (or other) indicator are dehydrated onto the concentration component and the conjugate pad, respectively. The user can simply apply the sample solution to the device, after which, components rehydrate and concentration of the target biomolecules occurs within the concentration component. Subsequently, the analytes will bind to the colorimetric indicator on the conjugate pad, and the resulting indicator-target complexes will be captured on the reaction pad as shown by a visible spot.
Figure 11:
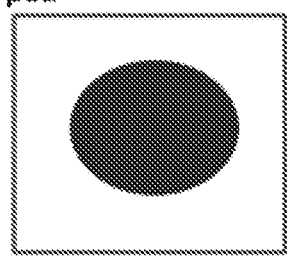
Figure 11:
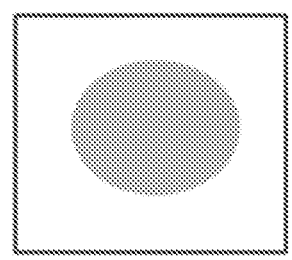
Figure 11:

In various embodiments the paper-based detection component can be in the form of a lateral-flow test strip (see, e.g., FIG. 1) or a flow-through device (spot test) (see, e.g. FIG. 11). In various embodiments both form factors may contain one or more of the following components:

Sample Pad

In certain embodiments a sample pad, when present, can connect the concentration component to the detection component. It can act as a filter that can remove debris, contaminants, and mucus from the collected fluid. It can also store dried reagents, and when rehydrated, these reagents can (i) adjust the solution for optimal detection conditions (pH, ionic strength, etc.); and (ii) break down mucus, glycoproteins, and other viscous materials in the collected specimen that may affect detection. Illustrative materials for the sample pad include, but are not limited to, cellulose, nitrocellulose, fiberglass, cotton, woven or nonwoven paper, etc. Reagents on the pad may include, but are not limited to, surfactants such as Triton X-100, Tween 20, or sodium dodecyl sulfate, etc.; polymers such as polyethylene glycol, poloxamer, polyvinylpyrrolidone (PVP), etc.; buffers such as phosphate-buffered saline, 4-(2-hydroxyethyl)-1-piperazineethanesulfonic acid (HEPES), Tris(hydroxymethyl)aminomethane (Tris), sodium borate, TRICINE, etc.; proteins such as albumin, etc.; enzymes such as protease, etc.; salts such as sodium chloride, sodium phosphate, sodium cholate, potassium phosphate, etc. In various embodiments these reagents can be applied to the sample pad by (i) soaking the paper material in the reagent solution, or (ii) through wicking the membrane via capillary flow. The treated sample pad can be dried by (i) air dry (let sit in room temperature); (ii) baking (place in high temperature using an oven or heating device); (iii) vacuum; or (iv) lyophilization.

Conjugate Pad

In various embodiments a conjugate pad, when present can contain dehydrated colorimetric indicators decorated with binding moieties that bind the target analyte(s). In certain embodiments the binding moieties are specific binding moieties that have high affinity towards the target analyte(s) (e.g., bacterium, fungus, virus, proteins, DNA, etc.). When the sample solution reaches the conjugate pad, the colorimetric indicators are rehydrated. The binding moieties on the colorimetric indicators can then bind to the target analyte(s) and the resulting complexes can flow to the reaction pad. In certain embodiments the colorimetric indicators can comprise metallic particles such as gold, silver particles, polymeric particles such as latex beads, and polystyrene particles encapsulating visible or fluorescent dyes. Illustrative materials material for the conjugate pad include, but are not limited to, cellulose, nitrocellulose, fiberglass, cotton, woven or nonwoven paper etc. In certain embodiments the colorimetric indicators can be applied and dehydrated onto the pad as described above.

Reaction Pad

In certain embodiments the reaction pad, when present, can comprise immobilized reagents, and when the immobilized reagents react with the sample solution, they may produce signals (e.g., visual signals) to indicate the presence or absence or quantity of the target analyte(s). Illustrative materials for the reaction pad include, but are not limited to cellulose, nitrocellulose, fiberglass, cotton, woven or nonwoven paper etc.

Lateral-Flow Format

In certain embodiments for a lateral-flow test strip, the reagents on the reaction pad will be immobilized in the form of lines perpendicular to the direction of flow to ensure all samples can interact with the immobilized reagents. The concentrations of the reagents can be optimized to control the signal intensities, and thus, control the sensitivity of the assay. For example, a semi-quantitative assay can be designed by immobilizing multiple lines of the same reagent with various concentrations. Each line therefore will yield signals only when a specific concentration of target biomolecules is reached. The concentration of the target biomolecules can then be interpreted by counting the number of lines that are visible (see, e.g., FIG. 2).

In addition, multiple lines of different reagents can be immobilized on the same strip to detect multiple target analyte(s). This allows the development of multiplex assays.

Flow-Through Format

In certain embodiments for the flow-through test, instead of lines, the reagents can be immobilized on the entire reaction pad. If the target analyte is present, it will bind to the colorimetric indicator on the conjugate pad and be trapped on the reaction pad as the indicator-target complex binds to the immobilized reagent. A visible spot would therefore appear if the target biomolecule is present. This test can be used if the sample volume is too low to wick up a lateral-flow test strip. The color intensity of the visible spot is correlated to the concentration of target biomolecules, while the size of the spot is correlated to the sample volume. In certain embodiments the concentration component can be placed directly on top of the flow-through test to remove the need for extracting and applying the concentrated samples to the detection component.

In various embodiments the immobilized reagents can comprise a specific antibody against the target analyte (primary antibody), antibodies against the primary antibody (secondary antibody), antigens, proteins, or antigen-protein conjugates. Illustrative materials for the reaction pad include, but are not limited to cellulose, nitrocellulose, fiberglass, cotton, woven and nonwoven paper etc. In various embodiments the reagents can be applied and dehydrated onto the pad as described above.

Sink

In certain embodiments the sink, when present, can comprise an absorbent pad that collect excess fluid and prevents back-flow which can affect the test performance. Illustrative materials for the sink include, but are not limited to cellulose, nitrocellulose, fiberglass, cotton, woven and nonwoven paper etc.

Signal Enhancement

As described above, in various embodiments the visible signal intensity can be enhanced to improve the sensitivity and/or accuracy of the detection assay. This can be performed by introducing additional development (signal enhancement) reagents to the reaction pad after the initial detection assay (analyte binding). As explained above, the probes and ATPS can be designed to first deliver the probes to a detection zone (e.g., in a leading phase or interface of an ATPS) followed by later delivery of a development reagent (e.g., in a lagging phase of an ATPS).

In certain embodiments the signal enhancement reagent can comprise a substrate that reacts with an enzyme that is decorated on the surface of, e.g., colorimetric indicator to form a strong visible product. By way of example, if the colorimetric indicator comprises a gold probe, the signal enhancement can be achieved by silver-enhancement labeling, where an enhancement reagent containing silver ion can be applied to the reaction pad where the gold probe is bound to the immobilized line/spot. In this scenario, the gold probes can act as nucleation sites so that silver can be deposited onto the particle, resulting in increased signal intensity. In these examples, the signal enhancement reagents can either be added separately after the initial detection assay, or stored/dehydrated on the paper device to be released automatically/manually.

In other illustrative, but non-limiting embodiments, the development reagent can be a substrate for an enzyme (e.g., of alkaline phosphatase, horse radish (or other) peroxidase, glucose oxidase, etc.) that reacts with the corresponding enzyme associated with or attached to the probe(s) to produce an enhanced detectable signal. Alternatively the developing reagent can comprise the enzyme while the substrate is attached to or associated with the probe(s).

The foregoing components and assay formats are illustrative and non-limiting. Using the teachings and examples, provided herein, numerous other assay devices and configurations will be available to one of skill in the art and some further design considerations and components are described below.

Lateral-Flow Assay (LFA) or Flow-Through (Spot) Assay

As explained above, in certain embodiments the devices and systems described herein are configured to provide a lateral-flow assay (LFA) or a flow-through (spot) assay for detection of the target analyte in a sample, where the LFA or spot assay is used alone or in conjunction with an aqueous two-phase system (ATPS). In some embodiments, the LFA or spot assay comprises a porous matrix into which is disposed the ATPS or components thereof, where the porous matrix is configured to and has porosity sufficient to allow the ATPS or components thereof to flow through the porous matrix when the ATPS or components thereof are in a fluid phase. Such porous LFA or spot assay devices are referred to herein as paper or paper fluidic devices and these terms are used interchangeably.

The term "paper", as used herein, is not limited to thin sheets from the pulp of wood or other fibrous plant substances although, in certain embodiments the use of such papers in the devices described herein is contemplated. Papers more generally refer to porous materials often in sheet form, but not limited thereto that allow a fluid to flow through.

In some embodiments, the porous matrix is sufficiently porous to allow the mixed phase solution, first phase solution and/or second phase solution of the ATPS, and/or target analyte, to flow through the LFA. In some embodiments, the porous matrix is sufficiently long and/or deep enough for the mixed phase solution, first phase solution and/or second phase solution, and/or target analyte, to flow vertically and/or horizontally through the LFA or spot assay device. In some embodiments, the first phase solution flows through the porous matrix at a first rate and the second phase solution flows through the porous matrix at a second rate, where the first rate and the second rate are different. In some embodiments of the LFA or spot assay the porous matrix comprises inter alia a material such as a scintered glass ceramic, a mineral, cellulose, a fiberglass, a nitrocellulose, polyvinylidene fluoride, a nylon, a charge modified nylon, a polyethersulfone, combinations thereof, and the like.

Concentrate-as-it-Flows

It was discovered that ATPSs can phase separate as the solution flows through a porous substrate (e.g., a paper) which we have termed "concentrate-as-it-flows". Moreover it was also discovered that flow through the paper significantly speeds up the concentration process. Based this phenomenon, the lateral-flow assay devices and the flow-through assay devices described herein can comprise a paper fluidic component that fully integrates the necessary components for a combined ATPS concentration with the LFA or flow-through detection. It was discovered that when a mixed ATPS solution is applied to certain paper materials, phase separation and analyte concentration occur as the solution flows. We also demonstrated that this phenomenon is preserved even when making an ATPS that had varying volume ratios, e.g., volume of the top phase divided by that of the bottom phase.

In some embodiments, the LFA or the spot assay (e.g., the concentration component of the spot assay) comprises a paper. In some embodiments, the paper comprises a sheet of porous material that allows fluid to flow through it. In some embodiments, the paper comprises a plurality of sheets of porous material that allows fluid to flow through them. In some embodiments, the paper comprises one or more materials such as cellulose, fiberglass, nitrocellulose, polyvinylidine fluoride, charge modified nylon, polyether sulfone, and the like. In some embodiments, the paper is a HI-FLOW PLUS® membrane.

In some embodiments, the paper is a woven paper. In some embodiments, the paper is a Whatman paper. In some embodiments, the Whatman paper comprises Whatman S17, Whatman MF1, Whatman VF1, Whatman Fusion 5, Whatman GF/DVA, Whatman LF1, Whatman CF1, and/or Whatman CF4.

In some embodiments, the paper concentrates the target analyte as the target analyte flows through the LFA or through the concentration component of a flow-through assay (e.g. a 'concentrate-as-it-flows'-based device). In some embodiments, the paper concentrates the target analyte as the target analyte flows through the LFA horizontally. In some embodiments, the paper concentrates the target analyte as the target analyte flows through the LFA or flow through assay vertically.

In some embodiments, the paper has a property that influences which phase solution will become the "leading fluid." By way of non-limiting example, when using PEG-salt ATPS, adding the solution to fiberglass paper will cause the salt phase to become the leading solution, while using cellulose paper will cause the PEG phase to become the leading solution. In some embodiments, phase separation within the paper accelerates phase separation. Also by way of non-limiting example, a micellar ATPS typically takes several hours to phase separate in a stagnant ATPS, but if applied to a paper strip, this phase separation occurs in minutes. This speeds up the diagnostic process by allowing the ATPSs, which are traditionally the rate-determining step in the process, to become more viable options for our rapid paper diagnostic assays. In some embodiments, the 'concentrate-as-it-flows' device comprises a PEG-salt ATPS (e.g., as illustrated in the Examples). In some embodiments, the 'concentrate-as-it-flows' device comprises a micellar ATPS. In some embodiments, the LFA device or the flow-through assay device comprises fiberglass paper or nitrocellulose paper.

In certain embodiments the LFA or flow-through assay device comprises a filter that removes debris (e.g., blood cells or other particulates), a sample pad where the sample comprising the target analyte is applied to the device, a detection zone (e.g. test line and control line) where there the target analyte binds and is detected, and an absorbance pad (e.g., a dry receiving paper) that can absorb excess sample and/or solutions applied to the LFA or flow through device (see, e.g., FIGS. 1 and 11). In some embodiments, the control line and/or test line is not a line per se, but a region or spot.

In some embodiments, the LFA comprises an LFA strip. The terms "LFA" and "LFA strip" are used interchangeably herein. In some embodiments, the LFA strip has a length greater than its width and depth. In some embodiments, the LFA is rectangular. In some embodiments, the LFA has a shape that is round, ovoid, square, polygonal, or irregular-shaped. In some embodiments, the LFA comprises a plurality of routes and/or junctions. In some embodiments, the LFA strip comprises the sample pad, detection zone and absorbance pad. In some embodiments, the detection zone is located between the sample pad and the absorbance pad, the absorbance pad wicking the sample with the target analyte away from the sample pad and toward the detection zone.

Sandwich Assay

In some embodiments, the LFA or flow-through (spot) assay device is configured to provide or run a sandwich assay (see e.g., FIG. 1, herein, and FIG. 1, bottom left, in copending PCT Application No: PCT/US2015/019297, filed on Mar. 6, 2015, which is hereby incorporated by reference for the LFA configurations described therein). In some embodiments, the sandwich assay comprises a capture moiety that binds the target analyte. In some embodiments, the device comprises a probe. In some embodiments, the probe comprises a detectable property (colorimetric, fluorescent, radioactive, etc.). In some embodiments, the probe comprises a binding moiety that interacts with the target analyte (e.g. an antibody). In some embodiments, the probe is added to the sample and binds the target analyte to form a probe-analyte complex.

Competition Assay

In some embodiments, the LFA comprises a competition assay. In some embodiments, the probe is added to the sample and binds the target analyte to form a probe-analyte complex. In some embodiments, the LFA comprises the target analyte immobilized on the test line. In some embodiments, the probe is saturated by the target analyte in the sample and the probe will not bind to the target analyte immobilized on the test line. In some embodiments, the absence the detectable signal on the test line indicates a positive result. In some embodiments, there is no target analyte present in the sample, and the probe binds to the target analyte on the test line, indicating a negative result. In some embodiments, the LFA comprises a probe capture moiety on a control line that interacts directly with the probe, and regardless of the presence of the target analyte in the sample, the probe can bind to the probe capture moiety and accumulate on the control line. In some embodiments, the probe becomes immobilized and detected on the control line, indicating a valid test. In some embodiments, a positive result (e.g., target analyte is present in sample) is indicated a detectable signal at the test line and the control line. In some embodiments, a negative result is indicated by a detectable signal at the control line.

In some embodiments, the probe-analyte complex is applied to the sample pad and flows through the LFA or through the flow-through device towards the absorbance pad. In some embodiments, the target analyte of the probe-analyte complex binds to the capture moiety. In some embodiments, the capture moiety is immobilized on a test line or a test region (e.g., a test layer in a flow-through device) and the probe-analyte complex becomes immobilized on the test line or in the test region. In some embodiments, the probe is colorimetric, and the test line or test region will exhibit a strong color (e.g. detectable signal) as the probe-analyte complex accumulates at the test line or in the test region, indicating a positive result. In some embodiments, there is no target analyte present in the sample, and the probe of the probe-analyte complex does not interact with the capture moiety, and the absence of the test line or signal in the test region indicates a negative result. In some embodiments, the LFA comprises a probe capture moiety on a control line (or in a control region, e.g., of a flow-through assay device) that interacts directly with the probe and/or the binding moiety, and thus, regardless of the presence of the target analyte in the sample, the probe/binding moiety binds to the probe capture moiety and accumulate on the control line or in the control region. In some embodiments, the probe capture moiety is a secondary antibody that binds the binding moiety, wherein the binding moiety is a primary antibody that binds that target analyte. In some embodiments, the probe becomes immobilized and detected on the control line or in the control region, indicating a valid test. In some embodiments, a positive result (e.g. target analyte is present in sample) is indicated by a detectable signal at the test line (or test region) and the control line (or control region). In some embodiments, a negative result is indicated by a detectable signal at the control line or in the control region.

Dehydrated ATPS in LFA or Flow-Through (Spot) Assay Device.

In some embodiments, the ATPS or components thereof and/or probes and/or development reagents are dehydrated on and/or in at least a first portion of the porous matrix comprising an LFA or in the concentration component of a flow-through assay device. In some embodiments, application of the sample to the device hydrates the ATPS, and/or probes and/or development reagent(s) thereby converting the ATPS or components thereof and/or probes and/or development reagent(s) to a fluid phase. Dehydration may make the device more user friendly as the user just needs to add the sample (e.g., saliva, blood, urine, vaginal fluid, seminal fluid, sputum, cerebrospinal fluid, lymph, or similar fluid) to the device. In some embodiments, a user only has to apply a solution of the sample to the strip to detect the presence/absence of the target analyte or to quantify the analyte. In some embodiments, the solution of the sample flows through the LFA or the flow-through device and the ATPS is resolubilized, triggering phase separation within the LFA or flow-through device and subsequent concentration of the target analyte.

In some embodiments, all the necessary components for a given ATPS are mixed to form a mixed solution, applied to the paper comprising the device (e.g., LFA or flow-through (spot) assay), and then dehydrated. When the sample solution is added to the dehydrated paper, the ATPS components are rehydrated as the sample flows, resulting in phase separation. In some ATPSs where the phase containing the concentrated analyte is less viscous, that phase will flow faster and the concentrated analyte will emerge in the leading fluid and will reach the detection zone of the LFA or flow-through assay to initiate detection. Additionally, the dehydrated ATPS component segment length (or thickness) and concentration can be adjusted for different applications.

In some embodiments, both (all) components of the ATPS are dehydrated on the LFA or in the flow-through assay (e.g., in the separation component). In some embodiments, a first ATPS component is dehydrated on (or in) the LFA or in the flow-through assay. In some embodiments, a second ATPS component is dehydrated on or in the LFA or flow through assay. In some embodiments, the first phase solution component and/or first ATPS component is dehydrated on a first portion of the LFA or in a first layer of the flow through assay (separation component). In some embodiments, the second phase solution component and/or second ATPS component is dehydrated on a second portion of the LFA or in a second layer of the flow-through assay (separation component). In some embodiments, the first portion and the second portion are same. In some embodiments, the first portion and the second portion are different. By way of non-limiting example, in a PEG-salt ATPS, the PEG and salt solutions can be dehydrated separately into different paper portions or segments (see, e.g., FIG. 16 of copending PCT Application No: PCT/US2015/019297, filed on Mar. 6, 2015, which is hereby incorporated by reference for the LFA configurations described therein) or in separate layers comprising, e.g., the separation component of a flow-through assay (see, e.g., FIG. 11). In some embodiments, dehydrating the first/second phase solution and/or ATPS component on different portions of the LFA or in different layers of the flow-through assay provides a more uniform concentration of the first/second phase solution components or ATPS components. In some embodiments, dehydrating the first/second phase solution components and/or ATPS components on different portions allows the first phase solution or ATPS component to flow in a first direction after hydration and the second phase solution and/or ATPS component to flow in a second direction after hydration, wherein the first and second directions are different. In some embodiments, the target analyte is concentrated in the first direction, but not the second direction. In some embodiments, the target analyte is concentrated in the second direction, but not the first direction. In some embodiments, dehydrating the first/second phase components and/or ATPS components on different portions allows the target analyte to flow in the first/second direction without requiring the sample to flow in the first/second direction. In some embodiments, dehydrating the first/second phase components and/or ATPS components on different portions allows the target analyte to flow faster, resulting in detection sooner. In some embodiments, dehydrating the first/second phase components and/or ATPS components on different portions allows for increased result reliability. In some embodiments, dehydrating the first/second phase components and/or ATPS components on different portions prevents aggregation of first/second phase solution components and/or ATPS components (e.g. PEG-salt ATPS). In some embodiments, the first/second phase component and/or ATPS component is dehydrated in multiple segments.

In some embodiments the first/second phase component and/or ATPS component is dehydrated in multiple segments, wherein the first/second phase component and/or ATPS component comprises a salt solution. In some embodiments the first/second phase component and/or ATPS component is dehydrated in multiple segments, wherein the first/second phase component and/or ATPS component does not comprise a polymer (e.g. PEG). In some embodiments, dehydrated PEG is not located near the detection zone because the PEG-rich phase can slow the flow within the detection membrane. In some embodiments, the LFA strip or the flow-through assay can comprise a blank spacer near the detection zone that does not contain PEG or salt.

In some embodiments, a probe (e.g., an analyte binding moiety and associated detection reagent/material) is provided in a probe buffer. In some embodiments, the probe buffer is dehydrated on the LFA or in the flow-through assay.

In some embodiments, dehydration of ATPS components improves the limit of detection compared to a device in which the ATPS components are added in liquid form. In some embodiments, the addition of liquid form ATPS components dilutes the sample solution from the subject. In some embodiments, dehydration of ATPS components allows for a distinct first phase solution and/or distinct second phase solution to develop during flow, concentrating the target analyte or probe-analyte complex in a small volume at the front of the leading fluid that will reach the test and control lines or the detection component of a flow-through assay. In some embodiments, concentrating the target analyte and or probe-analyte complex at the front of the leading fluid will decrease the time period necessary for detection.

Probes

In certain embodiments the systems and/or devices described herein and/or the methods described herein utilize a probe, where the probe comprises a binding moiety that binds the target analyte to form a probe-analyte complex.

In some embodiments, the target analyte alone partitions preferentially into the first phase solution or second phase solution or interface of the first phase solution and second phase solution. In some embodiments, the target analyte alone partitions extremely into the first phase solution or second phase solution or interface of the first phase solution and second phase solution.

In some embodiments, the target analyte alone does not partition preferentially into the first phase solution or second phase solution or interface of the first phase solution and second phase solution. In some embodiments, the target analyte alone does not partition extremely into the first phase solution or second phase solution or interface of the first phase solution and second phase solution.

In some embodiments, the probe-analyte complex partitions preferentially into the first phase solution or second phase solution or interface of the first phase solution and second phase solution, thereby causing the target analyte (of the probe-analyte complex) to partition preferentially into the first phase solution or second phase solution or interface of the first phase solution and second phase solution.

In some embodiments, the probe-analyte complex partitions extremely into the first phase solution or second phase solution or interface of the first phase solution and second phase solution, thereby causing the target analyte (of the probe-analyte complex) to partition extremely into the first phase solution or second phase solution or interface of the first phase solution and second phase solution.

In some embodiments, the phrase "partitions preferentially," when used with respect to the partitioning of the target analyte (or probe-analyte complex) to a first/second phase solution of the ATPS, indicates that a greater amount of the target analyte becomes disposed in a preferred phase solution than in another phase solution of the ATPS.

In some embodiments, the phrase "partitions extremely," when used with respect to the partitioning of the target analyte (or probe-analyte complex) to a first/second phase solution of the ATPS, indicates that about 90% or more of the target analyte becomes disposed in a preferred phase solution than in another phase solution of the ATPS.

In some embodiments, a greater amount of the target analyte partitions into the first phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the first phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the first phase solution.

In some embodiments, a greater amount of the analyte partitions into the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the second phase solution. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the second phase solution.

In some embodiments, a greater amount of the analyte partitions into the interface of the first phase solution and the second phase solution. In some embodiments, greater than about 50%, or greater than about 55%, or greater than about 60%, or greater than about 65%, or greater than about 70%, or greater than about 75%, or greater than about 80%, or greater than about 85%, or greater than about 90%, or greater than about 95%, or greater than about 98%, or greater than about 99% of the target analyte partitions into the interface. In some embodiments, greater than about 99%, or greater than about 99.1%, or greater than about 99.2%, or greater than about 99.3%, or greater than about 99.4%, or greater than about 99.5%, or greater than about 99.6%, or greater than about 99.7%, or greater than about 99.8%, or greater than about 99.9% of the target analyte partitions into the interface.

In some embodiments, the device comprises or is configured to utilize and/or the assay run on the device utilizes one probe (probes directed to a single analyte). In some embodiments, the device comprises or is configured to utilize and/or the assay run on the device utilizes at least two different probes (each directed to a different analyte), or at least 3 different probes, or at least 4 different probes, or at least 5 different probes, or at least 7 different probes, or at least 10 different probes, or at least 15 different probes, or at least 20 different probes.

In some embodiments, the probe comprises one or more of a synthetic polymer, a metal, a mineral, a glass, a quartz, a ceramic, a biological polymer, a plastic, and/or combinations thereof. In some embodiments, the probe comprises a polymer comprises a polyethylene, polypropylene, nylon (DELRIN®), polytetrafluoroethylene (TEFLON®), dextran and polyvinyl chloride. In some embodiments, the polyethylene is polyethylene glycol. In some embodiments, the polypropylene is polypropylene glycol. In some embodiments, the probe comprises a biological polymer that comprises one or more of a collagen, cellulose, and/or chitin. In some embodiments, the probe comprises a metal (e.g., that comprises one or more of gold, silver, platinum, palladium, cerium, titanium, stainless steel, aluminum, or alloys thereof). In some embodiments, the probe comprises a nanoparticle (e.g., a gold nanoparticle, a silver nanoparticle, etc.).

In some embodiments, the probe further comprises a coating. In some embodiments, the coating comprises polyethylene glycol or polypropylene glycol. In some embodiments, the coating comprises polypropylene. In some embodiments, the coating comprises polypropylene glycol. In some embodiments, the coating comprises dextran. In some embodiments, the coating comprises a hydrophilic protein. In some embodiments, the coating comprises serum albumin. In some embodiments, the coating has an affinity for the first phase solution or the second phase solution.

In some embodiments, the amount of target analyte in the sample is very low, such that the analyte needs to be substantially concentrated to enable detection by LFA or flow-through assay. In certain embodiments, substantial concentration is achieved at an interface, since the degree of analyte concentration is dependent on the volume of a phase in which the analyte partitions, or concentrates, and the "volume" at the interface is very small relative to the bulk phases.

In some embodiments, the probe partitions preferentially (or extremely) to the interface in order to drive the target analyte towards an interface. In some embodiments, the probe partitions preferentially (or extremely) to the interface due to their surface chemistry, wherein the surface chemistry is optimized to drive the probe to the interface. By way of non-limiting example, to drive the probe-analyte complex to the interface of a polymer-salt ATPS system, such as the polyethylene glycol-potassium phosphate (PEG/salt) system, the probes are conjugated to PEG (or PEGylated) to promote the PEG-PEG interaction with the PEG-rich phase, and/or are decorated with hydrophilic proteins to promote hydrophilic interactions with the PEG-poor phase. Using such an optimized probe decorated with specific antibodies or other molecules capable of binding to the target, the target analyte is captured and collected at the interface. Since the volume of the interface is very small, the analytes are highly concentrated and are applied to the subsequent LFA or detection region of the flow-through assay.

In some embodiments, gold nanoprobes (GNP) are prepared that are capable of partitioning to the interface of a PEG/salt ATPS, and operating conditions are optimized to allow for a fast phase separation time with a very high recovery of GNP/analyte.

In some embodiments, the probe-analyte complex partitions to a solid-liquid interface in the ATPS. In some embodiments, the solid is the wall of the chamber that contains the ATPS. In some embodiments, the solid is the collector of the assay device. In some embodiments, the solid comprises a solid polymer. In some embodiments, the solid polymer comprises polyethylene, cellulose, chitin, nylon, polyoxymethylene (DELRIN®), polytetrafluoroethylene (TEFLON®), polyvinyl chloride, or combinations thereof. In some embodiments, the solid polymer comprises polypropylene. In some embodiments, the probe-analyte complex sticks to the solid and is highly concentrated since it is present in the small volume at the solid-liquid interface, and not diluted by the volume of the bulk phases. In some embodiments, the bulk phase is removed without disrupting the concentrated analyte, and is collected by washing, with subsequent application to the LFA or to the flow-through assay device. In some embodiments, this approach significantly concentrates the analyte and allows collection without using an external force (e.g., magnet). Alternatively, the probe comprises a magnetic material and this approach is used with a magnet. In some embodiments, these probes are modified to be concentrated at the interface for extreme analyte concentration. As mentioned above, this approach can provide additional separation of the target analyte from other contaminants, which is nonspecifically concentrated by ATPS, through the use of a magnet. In some embodiments, the ATPS concentration enables the magnetic probe to work more efficiently, since the magnetic probe would first be concentrated into a very small volume at a specific location (the interface). Accordingly, a smaller magnet or a weaker magnetic field will be required to collect the concentrated analyte. In some embodiments, the combination of ATPS interface concentration with magnetic probes allows for the development of a more effective, rapid, and cheaper device compared to the current state-of-the-art.

Binding Moiety

In some embodiments, the binding moiety is a molecule that binds the target analyte (e.g., bacterium, fungus, virus, lectin, sugar, protein, DNA, etc.). In some embodiments, the binding moiety is a molecule that specifically binds the target analyte. In some embodiments, "specifically binds" indicates that the molecule binds preferentially to the target analyte or binds with greater affinity to the target analyte than to other molecules. By way of non-limiting example, an antibody will selectively bind to an antigen against which it was raised. Also, by way of non-limiting example, a DNA molecule will bind to a substantially complementary sequence and not to unrelated sequences under stringent conditions. In some embodiments, "specific binding" can refer to a binding reaction that is determinative of the presence of a target analyte in a heterogeneous population of molecules (e.g., proteins and other biologics). In some embodiments, the binding moiety binds to its particular target analyte and does not bind in a significant amount to other molecules present in the sample.

In some embodiments, the binding moiety comprises an antibody, a lectin, a protein, a glycoprotein, a nucleic acid, monomeric nucleic acid, a polymeric nucleic acid, an aptamer, an aptazyme, a small molecule, a polymer, a lectin, a carbohydrate, a polysaccharide, a sugar, a lipid, or any combination thereof. In some embodiments, the binding moiety is a molecule capable of forming a binding pair with the target analyte.

In some embodiments, the binding moiety is an antibody or antibody fragment. Antibody fragments include, but are not limited to, Fab, Fab', Fab'-SH, F(ab')$_2$, Fv, Fv', Fd, Fd', scFv, hsFv fragments, cameloid antibodies, diabodies, and other fragments described above.

In certain embodiments, the binding moiety comprises an aptamer. In some embodiments, the aptamer comprises an antibody-analogue formed from nucleic acids. In some embodiments, the aptamer does not require binding of a label to be detected in some assays, such as nano-CHEM-FET, where the reconfiguration would be detected directly. In some embodiments, the binding moiety comprises an aptazyme. In some embodiments, the aptazyme comprises an enzyme analogue, formed from nucleic acids. In some embodiments, the aptazyme functions to change configuration to capture a specific molecule, only in the presence of a second, specific, analyte.

In some embodiments, the probe comprises a detectable label. Detectable labels include any composition detectable by spectroscopic, photochemical, biochemical, immuno-chemical, electrical, optical, or chemical means. Illustrative useful labels include, but are not limited to, fluorescent nanoparticles (e.g., quantum dots (Qdots)), metal nanoparticles, including but not limited to gold nanoparticles, silver nanoparticles, platinum nanoparticles, fluorescent dyes (e.g., fluorescein, texas red, rhodamine, green fluorescent protein, and the like, see, e.g., Molecular Probes, Eugene, Oregon, USA), radiolabels (e.g., $^3$H, $^{125}$I, $^{35}$S, $^{14}$C, $^{32}$P, $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rb, $^{111}$Ag, and the like), enzymes (e.g., horse radish peroxidase, alkaline phosphatase and others commonly used in an ELISA), various colorimetric labels, magnetic or paramagnetic labels (e.g., magnetic and/or paramagnetic nanoparticles), spin labels, radio-opaque labels, and the like.

Alternatively or additionally, the probe can bind to another particle that comprises a detectable label. In some embodiments, the probes provide a detectable signal at the detection zone (e.g., test line, control line, test region, control region). In some embodiments, the detectable label/property comprises one or more of a colorimetric label/property, a fluorescent label/property, an enzymatic label/property, a colorigenic label/property, and/or a radioactive label/property. In some embodiments, the probe is a gold nanoparticle and the detectable property is a color. In some embodiments, the color is orange, red or purple.

Isothermal Amplification.

In certain embodiments the methods and/or devices described herein provide for amplification of a target nucleic acid without thermal cycling (e.g., isothermal amplification). Isothermal methods of nucleic acid amplification may be applied to double-stranded DNA. However, target nucleic acid molecules need not be limited to double-stranded DNA targets. For example, double-stranded DNA for use in isothermal amplification methods described herein may be prepared from viral RNA, or mRNA, or other single stranded RNA target sources, by reverse transcriptase. In further example, double-stranded DNA for use in non-cycling amplification methods described herein may be prepared from single-stranded DNA targets by DNA polymerase. In various embodiments such methods may be applied as an initial step, prior to application of isothermal amplification methods discussed below.

Isothermal amplification methods are well known to those of skill in the art. Such methods include, but are not limited to, a Self-Sustained Sequence Reaction (3SR), a Nucleic acid Based Transcription Assay (NASBA), a Transcription Mediated Amplification (TMA), a Strand Displacement Amplification (SDA), a Helicase-Dependent Amplification (HDA), a Loop-Mediated isothermal amplification (LAMP), stem-loop amplification, signal mediated amplification of RNA technology (SMART), isothermal multiple displacement amplification (IMDA), a single primer isothermal amplification (SPIA), and a circular helicase-dependent amplification (cHDA) (see, e.g., Notomi et al. (2000) *Nucl. Acids Res.* 28: e63; U.S. Pat. No. 6,743,605; Gill and Ghaemi (2008) *Nucleosides, Nucleotides, and Nucleic Acids*, 27: 224-243, and the like), Recombinase Polymerase Amplification (RPA) (see, e.g., Rohrman and Richards-Kortum (2012) *Lab Chip*, 12: 3082-3088, Wang et al. (2017) PLoS ONE 12(1): e0166903, and the like).

Components (e.g., enzymes) and kits for isothermal nucleic acid amplification are commercially available. Illustrative kits include, but are not limited to ISOAMP® III Universal tHDA kit from BIOHELIX®, loop-mediated isothermal amplification (LAMP), and TWISTAMP® recombinase polymerase amplification (RPA) from TwistDx.

Sample Collection

In various embodiments the sample to be assayed using the devices and methods described herein comprises a biological sample, an environmental sample, a food sample, etc. Illustrative biological samples include, but are not limited to biofluids such as blood or blood fractions, lymph, cerebrospinal fluid, seminal fluid, urine, oral fluid, vaginal fluid, and the like, tissue samples, plaque samples, endocervical swab samples, cell samples, tissue or organ biopsies or aspirates, histological specimens, and the like.

Where the biological sample comprises a tissue, in certain embodiments, the tissue may be lysed, homogenized, and/or ground and, optionally suspended in a sample solution. Where the biological sample comprise a biological fluid the fluid may be assayed directly or suspended in a sample solution prior to assay. In certain embodiments the sample solution may act to preserve or stabilize the biological sample or components thereof, and/or may act to extract or concentrate the biological sample or components thereof. In certain embodiments the sample solution may comprise a buffer, optionally containing preservatives, and/or enzymes (protease, nuclease, etc.), and/or surfactants, and/or ATPS components.

In certain embodiments, particular in point-of-care embodiments, the sample may be applied to the assay device immediately or after a modest time interval. In certain embodiments the sample may be delivered to a remote testing facility where the assay is run.

Methods and devices for collecting biological samples are well known to those of skill in the art, e.g., as illustrated below:

Oral Fluid Collection

Oral fluid can be collected by drooling into an empty vial, then transferring the fluid to the concentration component of the assay.

Oral fluid can also be collected using a swab and/or collection pad. For example, a swab or a collection pad can be placed in the user's mouth to soak up the oral fluid. The swab or the collection pad may contain compounds, such as peppermint extract, or a sour extract, to stimulate oral fluid production. The swab or collection pad can also act as a filter to remove food debris, contaminants, or mucus that may affect the downstream concentration and detection steps. In certain embodiments the oral fluid in the swab or collection pad can be extracted and mixed with aqueous two-phase components (ATPS) components for concentration. Extraction of the oral fluid from the collection device can be accomplished, for example, by applying physical pressure to the swab/pad to squeeze the fluid out, or by capillary action to introduce the fluid to the concentration component. Another configuration corresponds to the ATPS components being dehydrated downstream of the swab or collection pad so that no further user interaction is necessary.

Plaque Collection

Plaque can be collected by brushes, swabs, or picks on the surfaces of teeth, underneath gum, or between teeth. In certain embodiments the collected plaque can then be mixed in buffer or an ATPS solution for subsequent concentration.

Urine Collection

In various embodiments urine can be obtained with a collection cup. The collected urine can then be mixed in an ATPS solution for subsequent concentration, or applied directly onto the device if ATPS components are dehydrated in the concentration component. In a catheterized subject, urine can be obtained from the catheter or from the catheter receiving bag.

Vaginal/Endocervical Swab

Target analytes on the vaginal or cervical surface and/or in vaginal fluid can be collected by commercially available swabs. The collected swab can be placed in a buffer to release the target, or placed in the ATPS solution for direct concentration of the target biomolecules.

Blood Collection

Blood can be collected by pin (lancet) prick and collection in a capillary tube, by syringe, and the like.

Illustrative Analytes.

While essentially any analyte can be detected and/or quantified using the assay devices and methods described herein, in certain embodiments, the analyte is a clinically relevant analyte (e.g., a bacterium, a fungus, a protozoan, an amoeba, a virus, and the like).

Clinically relevant targets are well known to those of skill in the art.

Clinically Important Bacteria in Vaginal Fluids

Finding *Trichomonas vaginalis*, bacterial vaginosis and *actinomyces* infections in vaginal fluid or tissue samples, pap smears might be considered an indication for treatment without performing other diagnostic tests. Treatment of asymptomatic infections can prevent complications in selected patients. *Candida* can be a commensal bacteria in the vagina, therefore asymptomatic patients may not require treatment. Detection of a higher rate of *Trichomonas vaginalis* and *candida* infection in IUD users shows that IUDs can increase the risk of vaginal infections and associated complications.

Gonorrhea is a bacterial infection caused by the organism *Neisseria gonorrheae* and is a clinically important pathogen. Similarly, *Chlamydia*, caused by *Chlamydia trachomatis* and syphilis, caused by *Treponema pallidum* are important sexually transmitted disease whose rapid diagnosis is desirable.

Clinically Important Bacteria in Urine

*Escherichia coli* and *Proteus* sp. are bacterial pathogens that when found in urine are typically indicative of urinary tract infections.

Clinically Important Bacteria in the Oral Cavity

Gram-negative oral anaerobes have frequently been associated with periodontal disease, some species more frequently than others. Such anerobes include, but are not limited to *Prevotella* species (e.g., *Pr. intermedia, Pr. Nigrescens*, Pr. *Melaninogenica, Pr. Veroralis*, and the like) and *Porphyromonas* species (e.g., *Porph. Gingivalis*).

Additionally *Streptococcus mutans* has been implicated in the formation of dental caries. Additional clinically important bacteria of the instant disclosure include but are not limited to *Actinomyces viscosus, Lactobacillus casei, Staphylococcus aureus, Candida albicans, Lactobacillus acidophilus, Capnocytophaga gingivalis, Fusobacterium nucleatum*, or *Bacteroides fortsythus*.

It will be recognized that these pathogens are illustrative and non-limiting. One of skill will recognize that the assay devices and methods described herein can be used to detect and/or to quantify numerous other analytes including, but not limited to food toxins and/or pathogens, environmental toxins and/or pathogens, and the like. Thus, for example, the methods and devices described herein can be used to detect *E. coli* contamination of vegetables or other foods and/or any other food pathogens including, but not limited to those illustrated in Table 2.

TABLE 2

Illustrative, but non-limiting food pathogens that can be detected using the methods and devices described herein.

| Pathogen | Sources |
| --- | --- |
| *Campylobacter jejuni* | Raw milk, untreated water, raw and undercooked meat, poultry, or shellfish |
| *Clostridium botulinum* | Home-canned and prepared foods, vacuum-packed and tightly wrapped food, meat products, seafood, and herbal cooking oils |
| *Clostridium perfringens* | Meat and meat products |
| *Escherichia coli (E. coli)* | Meat (undercooked or raw hamburger), uncooked produce, raw milk, unpasteurized juice, contaminated water, contaminated fruits and vegetables |
| *Listeria monocytogenes* | Refrigerated, ready-to-eat foods (meat, poultry, seafood, and dairy - unpasteurized milk and milk products or foods made with unpasteurized milk) |
| Norovirus (Norwalk-like Virus) | Raw oysters, shellfish, cole slaw, salads, baked goods, frosting, contaminated water, and ice. It can also spread via person-to-person. |
| *Salmonella enteritidis* | Raw and undercooked eggs, raw meat, poultry, seafood, raw milk, dairy products, produce, and nuts (e.g., almonds) |
| *Salmonella typhimurium* | Raw meat, poultry, seafood, raw milk, dairy products, and produce |
| *Shigella* | Salads, milk and dairy products, raw oysters, ground beef, poultry, and unclean water |
| *Staphylococcus aureus* | Dairy products, salads, cream-filled pastries and other desserts, high-protein foods (cooked ham, raw meat and poultry), and humans (skin, infected cuts, pimples, noses, and throats) |

TABLE 2-continued

Illustrative, but non-limiting food pathogens that can be detected using the methods and devices described herein.

| Pathogen | Sources |
| --- | --- |
| *Vibrio cholerae* | Raw and undercooked seafood or other contaminated food and water. |
| *Vibrio parahaemolyticus* | Raw or undercooked fish and shellfish |
| *Vibrio vulnificus* | Raw fish and shellfish, especially raw oysters |
| *Yersinia enterocolitica* | Raw meat and seafood, dairy products, produce, and untreated water |

EXAMPLES

The following examples are offered to illustrate, but not to limit the claimed invention.

Example 1

Results for DNA Amplification

Materials and Methods

Preparation of tHDA-Only Reaction and the One-Pot Platform

Both the tHDA-only reaction and the one-pot system was designed to detect for *Escherichia coli* (*E. coli*) O157:H7. The conventional tHDA-only reaction—containing buffer, salts, nucleotide bases, gene-specific primers, and an enzyme mixture of helicase and polymerase—was prepared as a 50 µL reaction, according to manufacturer protocol. Whole *E. coli* cells were also directly added to the reaction. The suspension was heated at 65° C. for 1 hour before a sample was extracted and analyzed via gel electrophoresis. For the one-pot platform, the Triton X-100 surfactant was combined with tHDA reaction components in a single tube. Whole *E. coli* cells were also added, and the suspension was mixed to form a mixed micellar aqueous two-phase system (ATPS). The suspension was heated at 65° C. for 1 hour, which allowed for both phase separation and DNA amplification to occur. The top, micelle-poor phase was then extracted and analyzed via gel electrophoresis to confirm successful amplification.

Determining Partition Coefficients of DNA in the One-Pot System

A quantitative DNA partitioning study was performed to compare the concentration of DNA in both phases of the ATPS. For this study, genomic DNA from *E. coli* O157:H7, a 100 bp DNA fragment, and a 25 bp DNA fragment were selected as models mimicking the DNAs relevant to the one-pot system. A mixed micellar ATPS was made by combining Triton X-100 surfactant, the salts pertinent to the tHDA reaction, and the double-stranded DNAs. Mixed ATPSs were individually made for each of the three DNA types. These suspensions were heated at 65° C. for 1 hour to induce phase separation. Upon phase separation, both the micelle-poor top phase and micelle-rich bottom phase were extracted, and Quant-iT dsDNA fluorescent binding dye was added. The fluorescence intensity was then measured in a plate reader. Using a standard curve made with known DNA concentrations, DNA concentrations in the top and bottom phases were extrapolated.

Results and Discussions

Partitioning of DNA in the One-Pot Platform

From performing the DNA partitioning study, we determined the partition coefficients of each DNA type in the one-pot system. The partition coefficient was calculated by dividing the concentration of the DNA in the top phase by the concentration of DNA in the bottom phase. Of the three DNA types tested, the larger genomic DNA and 100 bp DNA fragment had similar partition coefficients that were found to be greater than 1 (FIG. 11). This indicated that DNA partitioned preferentially to the top, micelle-poor phase, and thereby concentrated in that phase. Meanwhile, the smaller 25 bp DNA fragment had a smaller partition coefficient close to the value of 1, indicating that the 25 bp DNA fragment partitioned more evenly between the two phases.

Improvement in Amplification and Detection of *E. coli* in the One-Pot Platform

Figure 12:
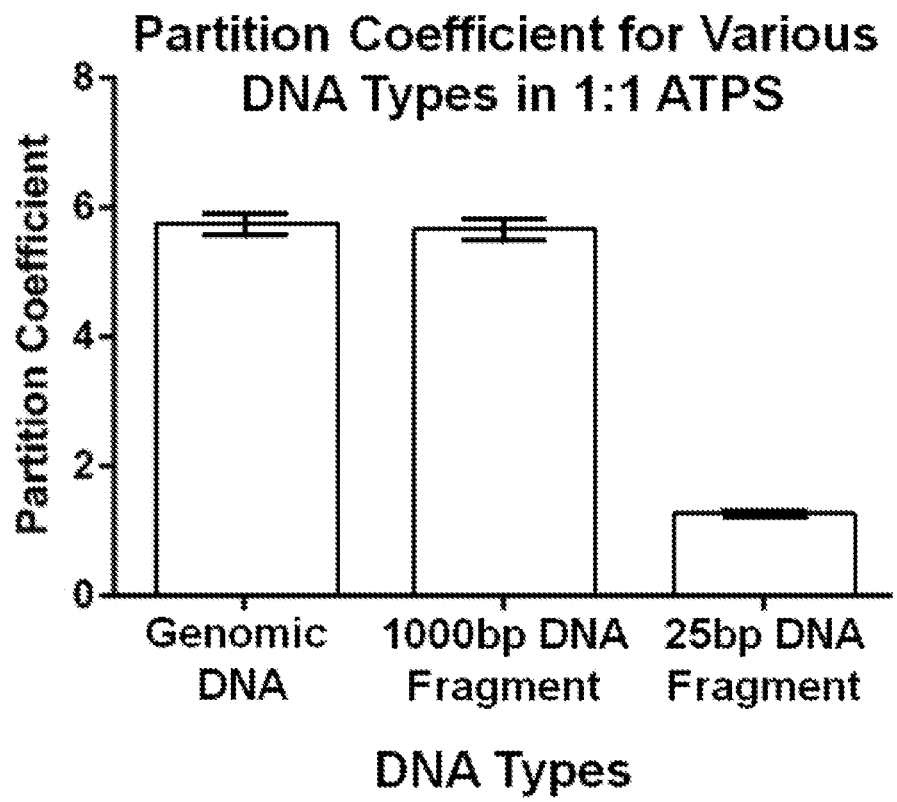
FIG. 12 shows partition coefficients of three DNA types in the one-pot system. Genomic DNA and the 100 bp DNA fragment partitioned preferentially to the top phase, while the smaller 25 bp DNA fragment partitioned evenly between the two phases.
Figure 13:
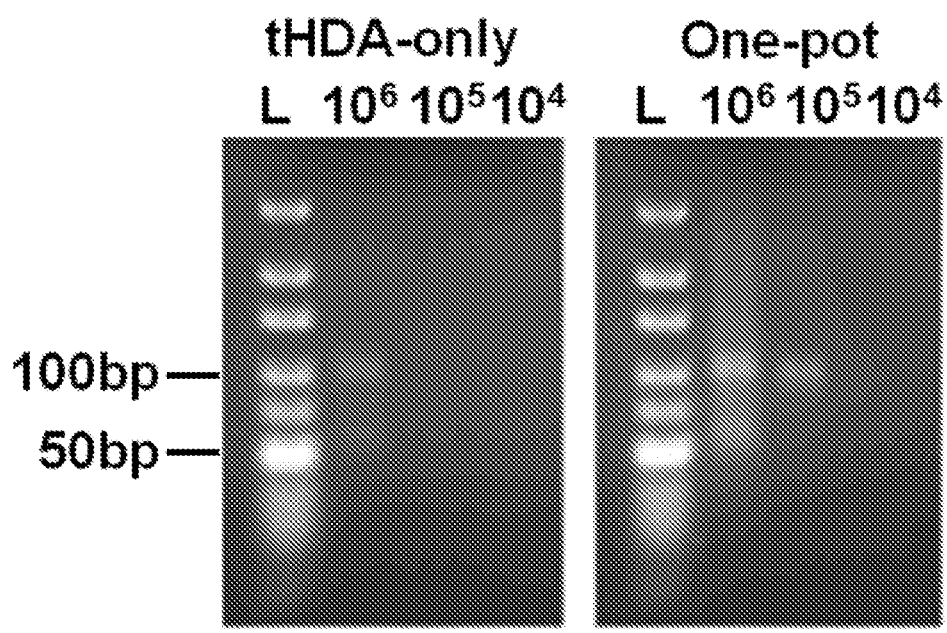
FIG. 13 shows results of DNA amplification with tHDA-only (left) and with the one-pot platform (right). The tHDA-only reaction successfully amplified DNA from a sample containing $10^6$ cfu/mL *E. coli*, while the one-pot platform successfully amplified DNA from samples containing $10^6$ and $10^5$ cfu/mL *E. coli*. "L" denotes the lanes containing the DNA ladder.

The tHDA reaction was found to be compatible with the micellar ATPS, resulting in the successful demonstration of the one-pot platform. Successful amplification was determined upon performing gel electrophoresis, indicated by the presence of a 100 bp band corresponding to the expected size of the amplified DNA region. To demonstrate improvement in amplification and detection using the one-pot system, amplification with the conventional tHDA-only reaction was compared to amplification performed in the one-pot platform. As visualized in FIG. 12, the conventional tHDA-only reaction successfully amplified DNA from cell samples containing $10^6$ cfu/mL; however, amplification was not achieved at lower cell concentrations. Alternatively, the one-pot platform successfully amplified DNA from cell samples containing $10^5$ cfu/mL, demonstrating a 10-fold improvement in the detection limit.

Example 2

Results for Enzymatic Signal Enhancement

Materials and Methods

Preparation of Assay Components

Aqueous two-phase systems (ATPS) were made from poly(ethylene glycol-ran-propylene glycol) and sodium sulfate salt in a 0.1M Tris buffer (pH 9). Alkaline phosphatase (ALP) and antibodies specific to *Chlamydia trachomatis* (CT) were conjugated to gold nanoparticles to create alkaline phosphatase-gold nanoprobes (ALP-GNPs). LFA test strips in the sandwich assay format were constructed by printing anti-CT antibodies as the test line and protein A as the control line on the nitrocellulose membrane. ALP-GNPs were dehydrated onto 3×10 mm glass fiber pads to create conjugate pads, which were placed immediately upstream of the membrane. A cotton fiber absorbent pad was placed downstream of the nitrocellulose membrane. In the conventional LFA, a single 3×10 mm glass fiber sample pad was placed upstream of the conjugate pad. In the enhanced LFA, a 3-D paper wick composed of four (7×15 mm) layers of glass fiber pads was placed upstream of the conjugate pad.

Demonstration of ATPS Automated Signal Enhancement

To run the signal enhanced assay, an LFA test strip with a 3-D paper wick was dipped into an ATPS that was spiked with CT to obtain an overall concentration of 3.2 ng/µL and the ALP substrates nitroblue tetrazolium/5-bromo-4-chloro-3-indolyl phosphate (NBT/BCIP). Photos were taken at 10, 30, and 50 minutes.

Improving Detection of CT using ATPS and Signal Enhancement

To run the conventional LFA, a test strip was dipped into a solution of various concentrations of inactivated CT in PBS. To run the signal enhanced assay, an LFA test strip with a 3-D paper wick was dipped into an ATPS that was spiked with various concentrations of inactivated CT and the ALP substrates nitroblue tetrazolium/5-bromo-4-chloro-3-indolyl phosphate (NBT/BCIP). Photos were taken at 30 minutes.

Results and Discussions

Demonstration of Automated Signal Enhancement

Figure 14:
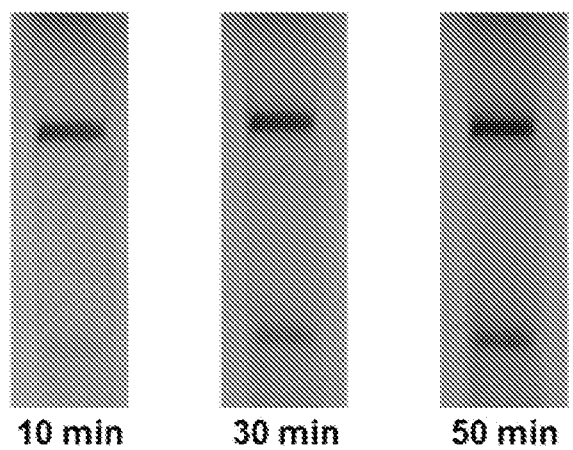
FIG. 14 shows time series images of the automated, signal enhanced LFA run at 3.2 ng/μL of CT. The darkening of the test and control lines over time with minimal background signal indicates the ability of the ATPS to be used to automate signal enhancement reactions.

When the LFA test strip with a 3-D paper wick was dipped into an ATPS containing CT and the NBT/BCIP substrates, the ATPS separated into its two macroscopic phases as it flowed through the test strip. First, the leading, salt-rich phase containing the concentrated CT bacteria solubilized the ALP-GNPs and delivered them to the LFA test zone where they could bind to the test and control lines, visualized by the appearance of two lines after 10 minutes. This was followed by the lagging, polymer-rich phase which delivered the NBT/BCIP substrates to initiate the signal enhancement reaction, which resulted in the darkening of both the test and control lines at 30 and 50 minutes (FIG. 14). Since the NBT/BCIP substrates partitioned favorably into the polymer-rich phase, premature signal enhancement was avoided.

Improving LFA Detection of CT Using Automated Signal Enhancement

Figure 15:
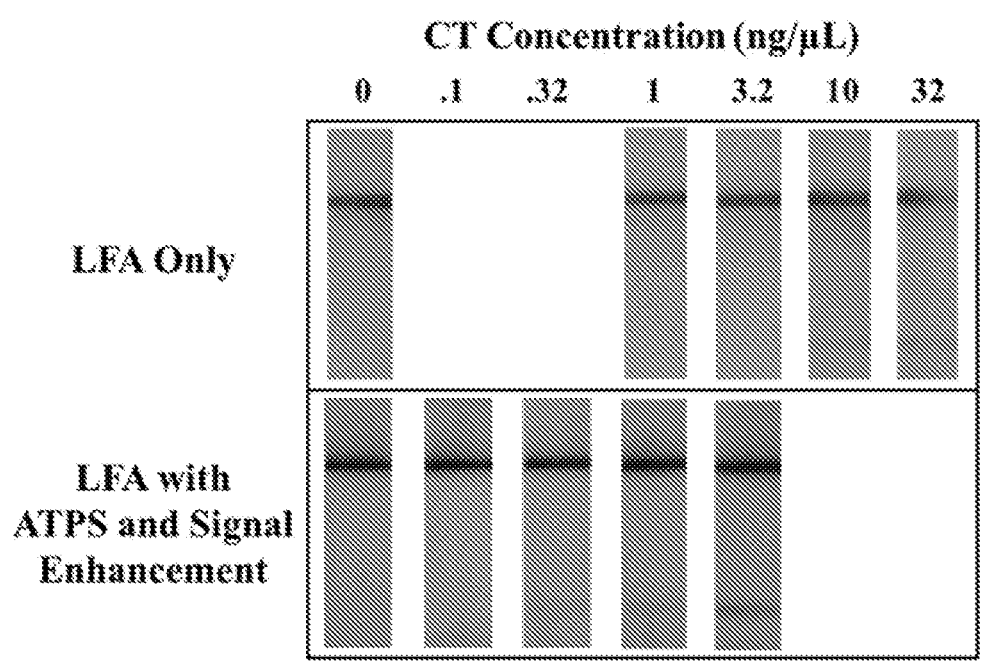
FIG. 15 shows that the LFA with ATPS and signal enhancement achieved a 30-fold improvement in the detection limit of CT. The conventional LFA detected CT at 10 ng/μL, while the enhanced LFA detected CT at 0.32 ng/μL.

After demonstrating the ability of the ATPS to automate a signal enhancement reaction on the LFA with minimal background development, we wanted to determine if this assay had an improved detection limit over the conventional LFA. First we identified the detection limit of the conventional LFA without the biomarker preconcentration and signal enhancement steps by testing dilutions of inactivated CT in PBS. Because a positive test is indicated by the presence of two lines in the sandwich assay format, our conventional LFA was able to successful detect CT at 10 ng/µL. To improve the detection limit of the conventional LFA, we then combined the LFA with the ATPS-automated biomarker preconcentration and signal enhancement step. When tested with various dilutions of CT, the enhanced LFA was able to detect CT at 0.32 ng/µL, demonstrating a 30-fold improvement over the conventional LFA (FIG. 15). This 30-fold improvement in detection limit is a result of the compounding improvements from both biomarker preconcentration and signal enhancement. With further optimization of both the biomarker preconcentration and signal enhancement components, the 30-fold improvement can be exceeded.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A device for the detection and/or quantification of an analyte in a sample, said device comprising:
    a lateral-flow assay (LFA) or a flow-through assay where said lateral flow assay and said flow-through assay each comprise a porous matrix configured to receive said sample and each comprises a binding moiety that binds and captures said analyte where said binding moiety is disposed in an LFA detection zone or a flow-through assay detection component;
    an aqueous two-phase system (ATPS) disposed in said lateral-flow assay or said flow-through assay, where said ATPS comprises a mixed phase solution that separates into a first phase solution and a second phase solution where, in use, said first phase solution becomes a leading phase and said second phase solution becomes a lagging phase as said ATPS passes through the porous matrix comprising said LFA or flow-through assay;
a probe that partitions into said first phase solution, where said probe binds said analyte, where in use, said probe binds said analyte when said analyte is present in a sample applied to said LFA or to said flow-through assay, to form a probe-analyte complex that partitions into said first phase solution in said leading phase of said ATPS; and
a development reagent that partitions into said second phase solution in said lagging phase of said ATPS, wherein of said probe and development reagent interact after said binding moiety binds said analyte and thereby immobilizes said probe-analyte complex in said device to provide a detectable signal that indicates the presence or amount of said analyte.

2. The device of claim 1, wherein the LFA comprises a conjugate pad, a test line comprising an antibody that binds said analyte, optionally a control line comprising a secondary antibody, optionally an absorbent pad, and optionally a sample pad.

3. The device of claim 1, wherein said ATPS is provided as components that form an ATPS when hydrated, where said ATPS components are provided in a dehydrated form on the lateral flow assay or in a concentration component of a flow-through assay where application of a sample rehydrates said components to form said ATPS.

4. The device of claim 3, wherein said probe is provided in a dehydrated form in the porous matrix comprising the lateral-flow assay or the flow-through assay before the device is contacted with the sample and said sample when applied to said device re-hydrates said probe which flows through said device in a first phase solution of said ATPS.

5. The device of claim 3, wherein said development reagent is provided in a dehydrated form on the lateral-flow assay or in a concentration component of a flow-through assay before the device is contacted with the sample and said sample, when applied to said device, re-hydrates said development reagent which flows through said device in a second phase solution of said ATPS.

6. The device of claim 1, wherein:
said probe is selected to extremely partition into a hydrophilic phase of said ATPS; or
said probe is selected to extremely partition into a hydrophobic phase of said ATPS.

7. The device of claim 1, wherein:
said development reagent is selected to extremely partition into a hydrophobic phase of said ATPS; or
said development reagent is selected to extremely partition into a hydrophilic phase of said ATPS.

8. The device of claim 1, wherein:
said probe partitions into a salt-rich phase of a polymer/salt ATPS and said development reagent partitions into a polymer-rich phase of said polymer/salt ATPS; or
said probe partitions into a micellar-poor phase of said ATPS and said development reagent partitions into a micellar-rich phase of said ATPS.

9. The device of claim 8, wherein said ATPS is a PEG/salt ATPS.

10. The device of claim 8, wherein said ATPS is a micellar ATPS.

11. The device of claim 10, wherein said probe partitions into a micellar-poor phase of said ATPS and said development reagent partitions into a micellar-rich phase of said ATPS.

12. The device of claim 1, wherein said probe comprises a binding moiety that binds to said target analyte, and wherein:
said target analyte comprises a moiety selected from the group consisting of a protein, a nucleic acid, a sugar or lectin, and a microorganism; and/or
said target analyte comprises a microorganism selected from the group consisting of a bacterium, a protozoan, a fungus, a virus, and an alga; and/or
said target analyte comprises a biomarker for a microorganism; and/or
said target analyte comprises a biomarker for a microorganism selected from the group consisting of a bacterium, a protozoan, a fungus, a virus, and an alga; and/or
said target analyte comprises a biomarker for a disease condition, a biomarker for food safety or hazard, or a biomarker for a bioterror agent.

13. The device of claim 12, wherein said binding moiety is selected from the group consisting of an antibody or antibody fragment, a lectin, a nucleic acid, and an aptamer.

14. The device of claim 1, wherein:
said probe comprises a material selected from the group consisting of a synthetic polymer, a metal, a mineral, a glass, a quartz, a ceramic, a biological polymer, and a plastic; and/or
said probe comprises a material selected from the group consisting of polyethylene, polypropylene, cellulose, chitin, nylon, polyoxymethylene, polytetrafluoroethylene, or polyvinyl chloride, dextran, polypropylene, or polyethylene glycol; and/or
said probe comprises a metal selected from the group consisting of gold, silver, iron, platinum, palladium, cerium, and titanium; and/or
said probe comprises a nanoparticle.

15. The device of claim 1, wherein said probe comprises an agent that can react with said development reagent to produce a detectable signal, and wherein:
said agent comprises an enzyme that reacts with a substrate to form a strong visible signal and said development reagent comprises said substrate; or
said agent comprises a substrate that reacts with an enzyme to form a strong visible product and said development reagent comprises said enzyme.

16. The device of claim 1, wherein:
said probe comprises a coating that has an affinity for the first phase solution or the second phase solution of said ATPS; and/or
said coating comprises a material selected from the group consisting of polypropylene glycol, polyethylene glycol, dextran, a hydrophilic protein, and a hydrophobic protein.

17. A kit for the detection and/or quantification of an analyte, said kit comprising:
a device of claim 1; and
a collection device for collecting a sample.

18. The device of claim 1, wherein said probe is selected to extremely partition into a hydrophobic phase of said ATPS.

19. The device of claim 18, wherein said development reagent is selected to extremely partition into a hydrophilic phase of said ATPS.

20. The device of claim 1, wherein said development reagent is selected to extremely partition into a hydrophilic phase of said ATPS.

21. The device of claim 1, wherein said ATPS is selected from the group consisting of a polymer/salt ATPS, a polymer/polymer ATPS, a micellar/polymer ATPS, and a micellar ATPS.

22. The device of claim 21, wherein said ATPS is a polymer/salt ATPS.

23. The device of claim 1, wherein said ATPS comprises said mixed phase solution applied to said device where said mixed phase solution contains said sample.

* * * * *